(12) United States Patent
Jiang et al.

(10) Patent No.: US 11,841,923 B2
(45) Date of Patent: Dec. 12, 2023

(54) PROCESSING METHOD, MODEL TRAINING METHOD, MEANS, AND STORAGE MEDIUM FOR SPINAL IMAGES

(71) Applicant: Alibaba Group Holding Limited, George Town (KY)

(72) Inventors: Tao Jiang, Hangzhou (CN); Yu Wang, Hangzhou (CN); Ying Chi, Beijing (CN); Lei Zhang, Shenzhen (CN); Xiansheng Hua, Hangzhou (CN)

(73) Assignee: Alibaba Group Holding Limited

(*) Notice: Subject to any disclaimer, the term of this patent is extended or adjusted under 35 U.S.C. 154(b) by 227 days.

(21) Appl. No.: 17/366,480

(22) Filed: Jul. 2, 2021

(65) Prior Publication Data

US 2022/0083821 A1 Mar. 17, 2022

(30) Foreign Application Priority Data

Jul. 6, 2020 (CN) .......................... 202010643038.6

(51) Int. Cl.
*G06K 9/00* (2022.01)
*G06F 18/21* (2023.01)
(Continued)

(52) U.S. Cl.
CPC ........ *G06F 18/2178* (2023.01); *G06F 18/214* (2023.01); *G06N 3/08* (2013.01);
(Continued)

(58) Field of Classification Search
CPC ........ G16H 50/20; G16H 30/20; G16H 30/40; G06N 3/08; G06N 3/045; G06N 3/082;
(Continued)

(56) References Cited

U.S. PATENT DOCUMENTS 8,885,976 B1 11/2014 Kuo
9,406,122 B2 8/2016 Hladuvka
(Continued)

FOREIGN PATENT DOCUMENTS

CN 107595387 A * 1/2018
CN 107977971 5/2018
(Continued)

OTHER PUBLICATIONS

Chen H. et al. (2015) Automatic Localization and Identification of Vertebrae in Spine CT via a Joint Learning Model with Deep Neural Networks. In: Navab N., Hornegger J., Wells W., Frangi A. (eds) Medical Image Computing and Computer-Assisted Intervention— MICCAI 2015. MICCAI 2015. Lecture Notes in Computer Science, vol. 9349. Springer, Cham. https://doi.org/10.1007/978-3-319-24553-9_63.

(Continued)

*Primary Examiner* — Xin Jia
(74) *Attorney, Agent, or Firm* — Van Pelt, Yi & James LLP

(57) ABSTRACT

The present application discloses a method, device, and system for processing a medical image. The method includes obtaining a source spinal image, identifying one or more vertebral bodies and one or more intervertebral discs comprised in the source spinal image, determining the vertebral body recognition results corresponding to the one or more vertebral bodies and the intervertebral disc recognition results corresponding to the one or more intervertebral discs, and determining target recognition results corresponding to the source spinal image based at least in part one on one or more of the vertebral body recognition results and the intervertebral disc recognition results.

21 Claims, 17 Drawing Sheets

(51) Int. Cl.
*G06T 7/73* (2017.01)
*G16H 30/40* (2018.01)
*G06N 3/08* (2023.01)
*G06T 7/00* (2017.01)
*G06F 18/214* (2023.01)

(52) U.S. Cl.
CPC .............. *G06T 7/0014* (2013.01); *G06T 7/73* (2017.01); *G16H 30/40* (2018.01); *G06T 2200/24* (2013.01); *G06T 2207/20076* (2013.01); *G06T 2207/20081* (2013.01); *G06T 2207/20084* (2013.01); *G06T 2207/30012* (2013.01); *G06V 2201/033* (2022.01)

(58) Field of Classification Search
CPC ................... G06T 7/0012; G06T 7/143; G06T 2207/10088; G06T 2207/20084; G06T 2207/20081; G06T 2207/30016; G06T 7/11
See application file for complete search history.

(56) References Cited

U.S. PATENT DOCUMENTS

| | | |
|---|---|---|
| 9,558,543 B2 | 1/2017 | Hsieh |
| 9,916,655 B2 | 3/2018 | Stampanoni |
| 2006/0098897 A1 | 5/2006 | Dewaele |
| 2011/0058720 A1 | 3/2011 | Lu |
| 2017/0076430 A1 | 3/2017 | Xu |
| 2018/0316864 A1 | 11/2018 | Molgaard |
| 2019/0005660 A1* | 1/2019 | Kinoshita ................ G06T 7/74 |

FOREIGN PATENT DOCUMENTS

| | | | |
|---|---|---|---|
| CN | 108038860 | | 5/2018 |
| CN | 105433988 B | * | 10/2018 |
| CN | 109360213 A | * | 2/2019 |
| CN | 109493317 | | 3/2019 |
| CN | 109523523 A | * | 3/2019 |
| EP | 2639763 | | 10/2015 |
| EP | 3005289 | | 7/2017 |
| WO | 2020199528 | | 10/2020 |
| WO | 2021017297 | | 2/2021 |

OTHER PUBLICATIONS

Neubert et al. Automated Detection, 3D Segmentation and Analysis of High Resolution Spine MR Images Using Statistical Shape Models. Published Nov. 30, 2012 • © 2012 Institute of Physics and Engineering in Medicine. Physics in Medicine & Biology, vol. 57, No. 24: DOI: 10.1088/0031-9155/57/24/8357.

* cited by examiner

PROCESSING METHOD, MODEL TRAINING METHOD, MEANS, AND STORAGE MEDIUM FOR SPINAL IMAGES

CROSS REFERENCE TO OTHER APPLICATIONS

This application claims priority to People's Republic of China Patent Application No. 202010643038.6 entitled PROCESSING METHOD, MODEL TRAINING METHOD, MEANS, AND STORAGE MEDIUM FOR SPINAL IMAGES filed Jul. 6, 2020 which is incorporated herein by reference for all purposes.

FIELD OF THE INVENTION

The present application relates to a field of computer technology. In particular, the present application relates to a processing method, model training method, means, and storage medium for spinal images.

BACKGROUND OF THE INVENTION

Lumbar degenerative disease is a major type of bone disease common among the elderly. The number of patients is relatively large, and a trend towards younger patients has become increasingly obvious. Serious lumbar degenerative disease may cause lumbocrural pain and even paralysis, with an adverse impact on life skills and quality of life. However, in spite of having a huge number of such patients, primary care institutions lack sufficient orthopedists. There is an urgent need for orthopedists or for another method for diagnosing problems arising with a patient's lumber system. Therefore, in order to alleviate the primary care supply-demand imbalance, a recognition method capable of accurately and quickly recognizing lumbar pathologic change may be implemented.

BRIEF DESCRIPTION OF THE DRAWINGS

Various embodiments of the invention are disclosed in the following detailed description and the accompanying drawings.

The drawings described here are intended to further the understanding of the present application and form a part of the present application. The illustrative embodiments of the present application and the descriptions thereof are intended to explain the present application and do not constitute inappropriate limitation to the present application. Among the drawings.

DETAILED DESCRIPTION

Figure 1:
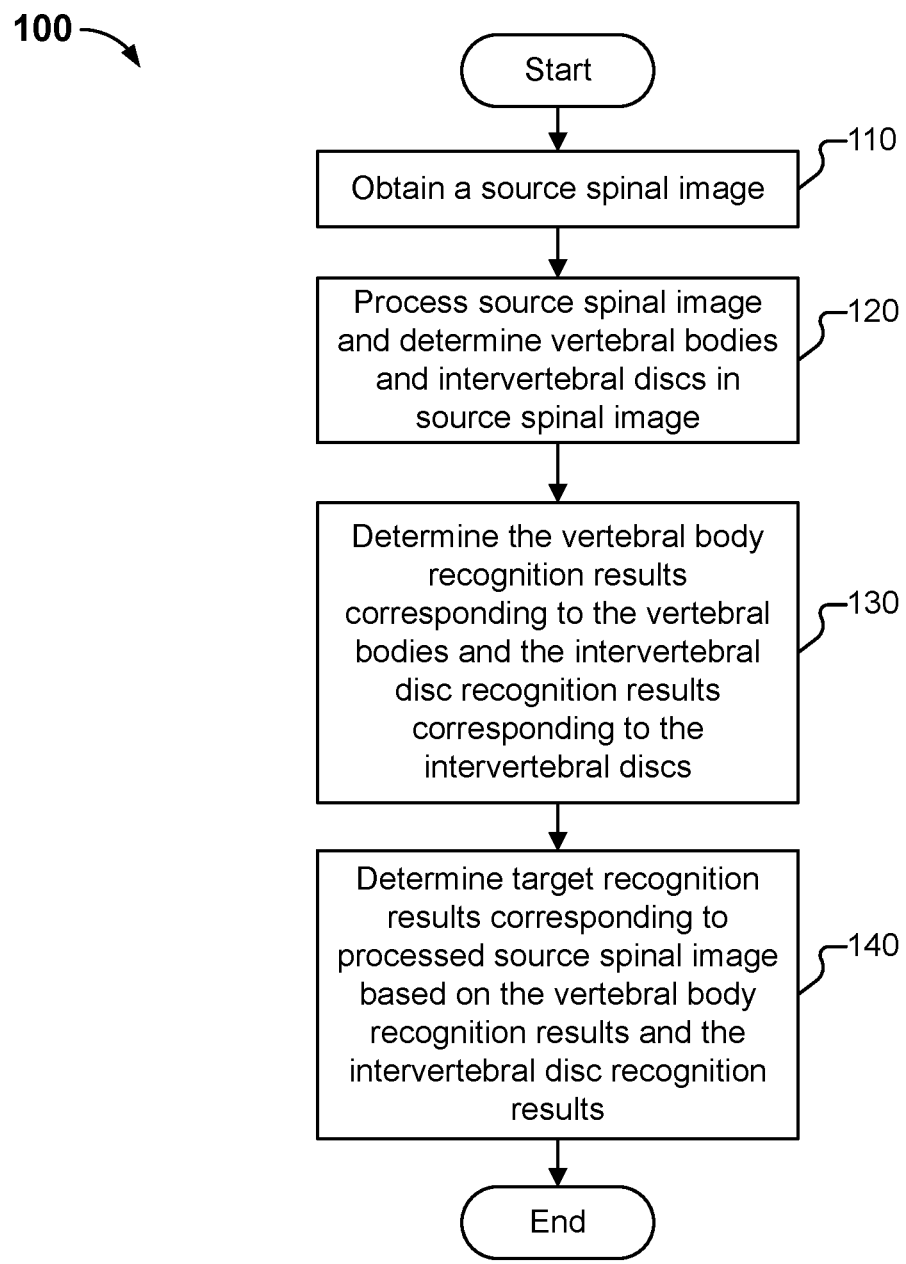
FIG. 1 is a flowchart of a method for processing a spinal image according to various embodiments of the present application.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The descriptions below set forth many particular details for a full understanding of the present application. However, the present application can be implemented in many ways other than those described here. A person skilled in the art may extend it similarly without violating the meaning of the present application. Therefore, the present application is not limited by the specific embodiments disclosed below.

As used herein, a "terminal" generally refers to a device comprising one or more processors. A terminal may also be referred to herein as a user equipment (UE). A terminal may be a device used (e.g., by a user) within, or connected to, a network system and used to communicate with one or more servers. According to various embodiments of the present disclosure, a terminal includes components that support communication functionality. For example, a terminal can be a smart phone, a server, a machine of shared power banks, information centers (such as one or more services providing information such as traffic or weather, etc.), a tablet device, a mobile phone, a video phone, an e-book reader, a desktop computer, a laptop computer, a netbook computer, a personal computer, a Personal Digital Assistant (PDA), a Portable Multimedia Player (PMP), a mobile medical device, a camera, a wearable device (e.g., a Head-Mounted Device (HMD), electronic clothes, electronic braces, an electronic necklace, an electronic accessory, an electronic tattoo, or a smart watch), a kiosk such as a vending machine, a smart home appliance, vehicle-mounted mobile stations, a door lock, a water meter, or an electricity meter, or the like. The terminal may be implemented as an Internet of Things (IoT) device. A terminal may run various operating systems.

Lumbar degenerative disease is a major type of bone disease common among the elderly. The number of patients is relatively large, and a trend towards younger patients has become increasingly obvious. Serious lumbar degenerative disease may cause lumbocrural pain and even paralysis, with an adverse impact on life skills and quality of life. However, in spite of having a huge number of such patients, primary care institutions lack sufficient orthopedists. Therefore, in order to alleviate the primary care supply-demand imbalance, there is an urgent need for a recognition method capable of accurately and quickly recognizing lumbar pathologic change.

Some methods may be implemented to rapidly recognize lumbar pathologic changes. The methods may include obtaining a lumbar image, performing a segmentation processing on the lumbar image, obtaining images of regions corresponding to each vertebral body and intervertebral disc, and performing analytical processing separately on the extracted region images to recognize vertebral body pathologic change information and intervertebral disc pathologic change information corresponding to each region image.

However, the method for rapidly recognizing lumbar pathologic changes described above generally requires that the image regions corresponding to each vertebral body and intervertebral disc be first recognized and segmented, which adds data processing steps thus causing the data processing process to become more complex, and increases the data processing volume, which hinders improvements to data processing efficiency.

Various embodiments include a method, a model training method, a means, and a storage medium for processing spinal images. In some embodiments, the method obtains a to-be-processed spinal image (also referred to herein as a "source image" or "source spinal image") and then performs analytical processing on the source spinal image to recognize vertebral bodies and intervertebral discs included in the source spinal image. The method may include determining vertebral body recognition results corresponding to the vertebral bodies and intervertebral disc recognition results corresponding to the intervertebral discs. The method may include using the vertebral body recognition results and intervertebral disc recognition results as basis for determining target recognition results corresponding to the source spinal image. Various embodiments effectively achieve recognition of vertebral bodies and intervertebral discs without having to segment the source spinal image. Various embodiments not only decreases the number of data processing steps and reduces data processing volume, but also, batch processing of multiple source spinal images may be implemented, thus helping to alleviate the primary care supply-demand imbalance while also improving the quality and efficiency of analytical processing of source spinal images.

FIG. 1 is a flowchart of a method for processing a spinal image according to various embodiments of the present application.

Referring to FIG. 1, process 100 may be implemented by a terminal. For example, process 100 may be implemented by an image capturing device such as a mobile phone, a tablet, etc. As another example, process 100 may be implemented in connection with medical imaging (e.g., by a terminal or server associated with processing images captured by a medical device such as an x-ray, an magnetic resonance imaging (MM), etc.). Process 100 may be implemented in connection with other imaging/image capturing technologies.

At 110, a source spinal image is obtained. In some embodiments, a server obtains the source spinal image. For example, the server may be obtained based on an input corresponding to a user selection (e.g., an input to a client terminal and sent to the server). The source spinal image may be uploaded to the server, or the server may retrieve the source spinal image from a database, such as a database of patients to medical scans, etc. The server may host a web-service such as an image-processing service. In some embodiments, a terminal obtains the source image. For example, a mobile terminal may obtain the source spinal image in response a user selection. The source spinal image may be obtained in response to image capture using a camera application, etc.

The spine is a human anatomical structure composed of multiple, sequentially connected vertebral bodies and intervertebral discs. A spine may specifically include at least one of the following: cervical vertebrae, thoracic vertebrae, and lumbar vertebrae. The cervical vertebrae, thoracic vertebrae, and lumbar vertebrae are located in different positions on the spine. Different positions (e.g., relative locations) on the spine may comprise different numbers of vertebral bodies and intervertebral discs. For example, the cervical vertebrae may include 7 vertebral bodies and 5 intervertebral discs; the thoracic vertebrae may include 12 vertebral bodies and 12 intervertebral discs; and the lumbar vertebrae may include 5 vertebral bodies and 6 intervertebral discs.

In addition, a source spinal image may comprise to an image obtained through an image capture of the spine that is to be recognized (e.g., a spine that is to be identified and/or analyzed). Specifically, the source spinal image may include at least one of the following: a magnetic resonance imaging (MM) image, an X-ray image, a computed tomography (CT) image, a B ultrasound image, etc. Various other types of images may correspond to the source spinal image. For example, various technologies may be implemented to image a patient's body/spine.

Various embodiments impose no restrictions as to the specific method and/or technology used in connection with capturing or obtaining the source spinal images. For example, the source spinal image may correspond to image data obtained after performing a test on the user with a preset testing apparatus. Various embodiments may obtain the source spinal image via the preset testing apparatus. In some embodiments, the source spinal image may be stored in a preset area (e.g., locally at a terminal or server, in a database accessible via the terminal or server, etc.). The device that processes the source spinal image may acquire the source spinal image by accessing the preset area.

At 120, the source spinal image is processed and vertebral bodies and intervertebral discs included in the source spinal image are determined. In some embodiments, the vertebral bodies and intervertebral discs included in the source spinal image are determined based at least in part on one or more characteristics associated with a vertebral body and/or intervertebral disc, such as in a mapping of characteristics to a vertebral body and/or intervertebral disc. The one or more characteristics may include one or more of shape, color, size, relative location, relative characteristics of the vertebral body and/or intervertebral disc (e.g., a relative characteristic of each vertebral body and/or intervertebral disc), etc.

After a source spinal image is obtained, the source spinal image may undergo analytical processing to recognize the vertebral bodies and intervertebral discs included in the source spinal image. For example, in response to the source spinal image being captured (e.g., by an imaging technology), a terminal or server may process the source spinal image to identify/determine vertebral bodies and intervertebral discs included in the source spinal image. The vertebral bodies may include at least one of the following: spinal vertebral bodies, thoracic vertebral bodies, and lumbar vertebral bodies. The intervertebral discs may correspondingly include at least one of the following: spinal intervertebral discs, thoracic intervertebral discs, lumbar intervertebral discs, etc.

Various embodiments do not impose restrictions on how the vertebral bodies and intervertebral discs included in the source spinal image are recognized. A person skilled in the art may implement settings based on specific application and design needs e.g., pre-train a machine learning model for recognizing vertebral bodies and intervertebral discs included in a spinal image and subject the source spinal image to analytical processing by the machine learning model in order to recognize vertebral bodies and intervertebral discs included in the source spinal image. In some embodiments, in response to obtaining vertebral body features corresponding to the vertebral bodies and intervertebral disc features corresponding to the intervertebral discs, the vertebral body features may be used as a basis to recognize vertebral bodies included in the source spinal image, and the intervertebral disc features may be used as a basis to recognize intervertebral discs included in the source spinal image. Various other processes or technologies may be implemented to recognize vertebral bodies and intervertebral discs included in the source spinal image. For example, such other processes or technologies may comprise the ability to ensure accurate and reliable recognition of the vertebral bodies and intervertebral discs in the source spinal image.

In some examples, after vertebral bodies and intervertebral discs included in the source spinal image are recognized, the recognized vertebral bodies and intervertebral discs may be labeled according to a preset labeling sequence, syntax, etc. According to various embodiments, because different parts of the spinal column may correspond to different numbers of vertebral bodies and intervertebral discs, vertebral bodies and intervertebral discs in different positions may be labeled according to a preset labeling sequence. For example, in the case of lumbar vertebrae, the 5 vertebral bodies may be labeled in ascending order as: L5, L4, L3, L2, and L1; the six intervertebral discs may be labeled in ascending order as: L5-S1, L4-L5, L3-L4, L2-L3, L1-L2, and T12-L1, wherein the intervertebral disc T12-L1 is the intervertebral disc between the 12th thoracic vertebra and the first lumbar vertebra, the intervertebral disc L1-L2 is the intervertebral disc between the first lumbar vertebra and the second lumbar vertebra, the intervertebral disc L2-L3 is the intervertebral disc between the second lumbar vertebra and the third lumbar vertebra, and the intervertebral disc L5-S1 is the intervertebral disc between the fifth lumbar vertebra and the first sacral vertebra.

Similarly, the 7 vertebral bodies and 5 intervertebral discs included in the cervical vertebrae may be labeled in descending order. The thoracic vertebrae have a more complex structure. Therefore, after vertebral bodies and intervertebral discs are recognized as being included among the thoracic vertebrae, a positioning label operation input by the user may be obtained (e.g., received) for any vertebral body or intervertebral disc among the thoracic vertebrae and a labeling operation may be performed based on said positioning label operation for vertebral bodies and intervertebral discs included among the thoracic vertebrae.

At 130, vertebral body recognition results corresponding to the vertebral bodies and the intervertebral disc recognition results corresponding to the intervertebral discs are determined.

After a vertebral body is obtained (e.g., determined), analytical processing may be performed with respect to the vertebral body in connection with determining the corresponding vertebral body recognition result. After an intervertebral disc is obtained (e.g., determined), analytical processing may be performed with respect the intervertebral disc in connection with determining the corresponding intervertebral disc recognition result.

Figure 3:
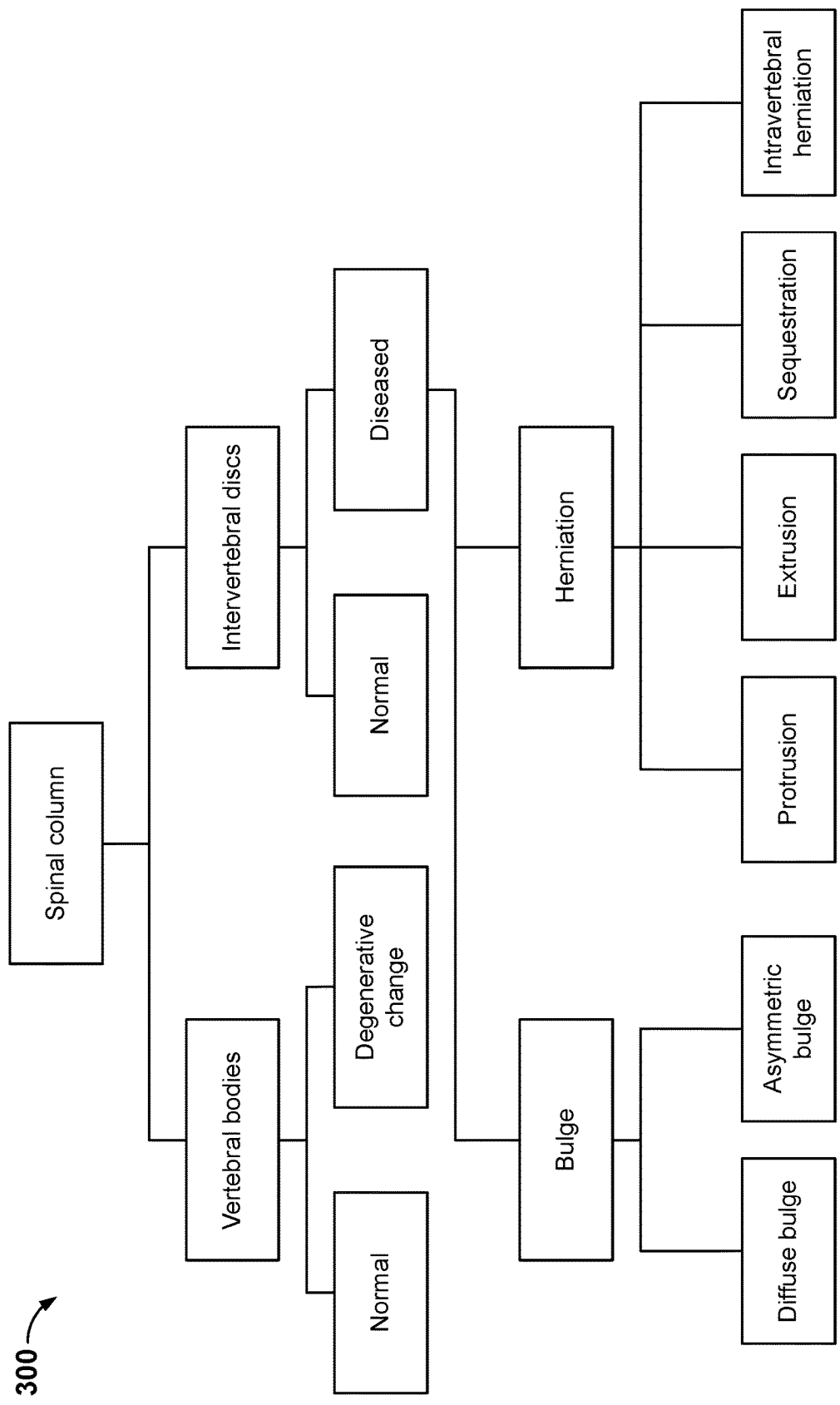
FIG. 3 is a diagram of a type of vertebral body recognition results and intervertebral disc recognition results according to various embodiments of the present application.

FIG. 3 is a diagram of a type of vertebral body recognition results and intervertebral disc recognition results according to various embodiments of the present application.

Referring to FIG. 3, a mapping of spinal information 300 may be used in connection with analyzing a source spinal image. According to various embodiments, mapping of spinal information 300 may be used in connection with determining performing a diagnosis with respect to the spine (or part of the spine) captured in the source spinal image. For example, a recognition result may be determined based at least in part on the mapping of spinal information 300.

According to various embodiments, as shown in FIG. 3, if the vertebral bodies include lumbar vertebral bodies and intervertebral discs include lumbar intervertebral discs, the vertebral body recognition results may include: normal vertebral body and vertebral body with degenerative change; and the intervertebral disc recognition results may include: normal intervertebral disc and pathologic change of intervertebral disc. This pathologic change of intervertebral disc may include: intervertebral disc bulge and intervertebral disc herniation. Intervertebral disc bulge may include diffuse bulge and asymmetric bulge. Intervertebral disc herniation may include protrusion, extrusion, sequestration, and intervertebral herniation.

At 140, a target recognition results corresponding to the source spinal image based at least in part on the vertebral body recognition results and the intervertebral disc recognition results.

After the vertebral body recognition results and intervertebral disc recognition results are obtained (e.g., determined), analytical processing may be performed with respect to the vertebral body recognition results and/or analytical processing may be performed with respect to the intervertebral disc recognition results in connection with determining target recognition results corresponding to the source spinal image. In some embodiments, the vertebral body recognition results and the intervertebral disc recognition results may be deemed the target recognition results corresponding to the source spinal image.

In some examples, the target recognition results may include a probability map having the same resolution as the source spinal image. The probability map may include vertebral body recognition probabilities corresponding to the vertebral body recognition results and intervertebral disc recognition probabilities corresponding to the intervertebral disc recognition results. By configuring the target recognition results as a probability map having the same resolution as the source spinal image, user editing operations directed at the target recognition results may be implemented or facilitated and the source spinal image, thus further improving the utility of the method.

According to various embodiments, processing of a spinal image comprises obtaining a source spinal image, vertebral bodies and intervertebral discs included in the source spinal image are identified or determined, and vertebral body recognition results corresponding to vertebral bodies and intervertebral disc recognition results corresponding to intervertebral discs are determined. In some embodiments, the vertebral body recognition results and the intervertebral disc recognition results are used in connection with (e.g., as a basis for) determining target recognition results corresponding to the source spinal image. Thus, various embodiments can effectively recognize vertebral bodies and intervertebral discs without having to segment the source spinal image. Various embodiments may not only decrease the number of data processing steps and reduce data processing volume, but also, implement batch processing of multiple source spinal images, thus helping to alleviate the primary care supply-demand imbalance while also improving the quality and efficiency of source spinal image analytical processing and further increasing the utility of the method to the benefit of market promotions and applications.

Figure 2:
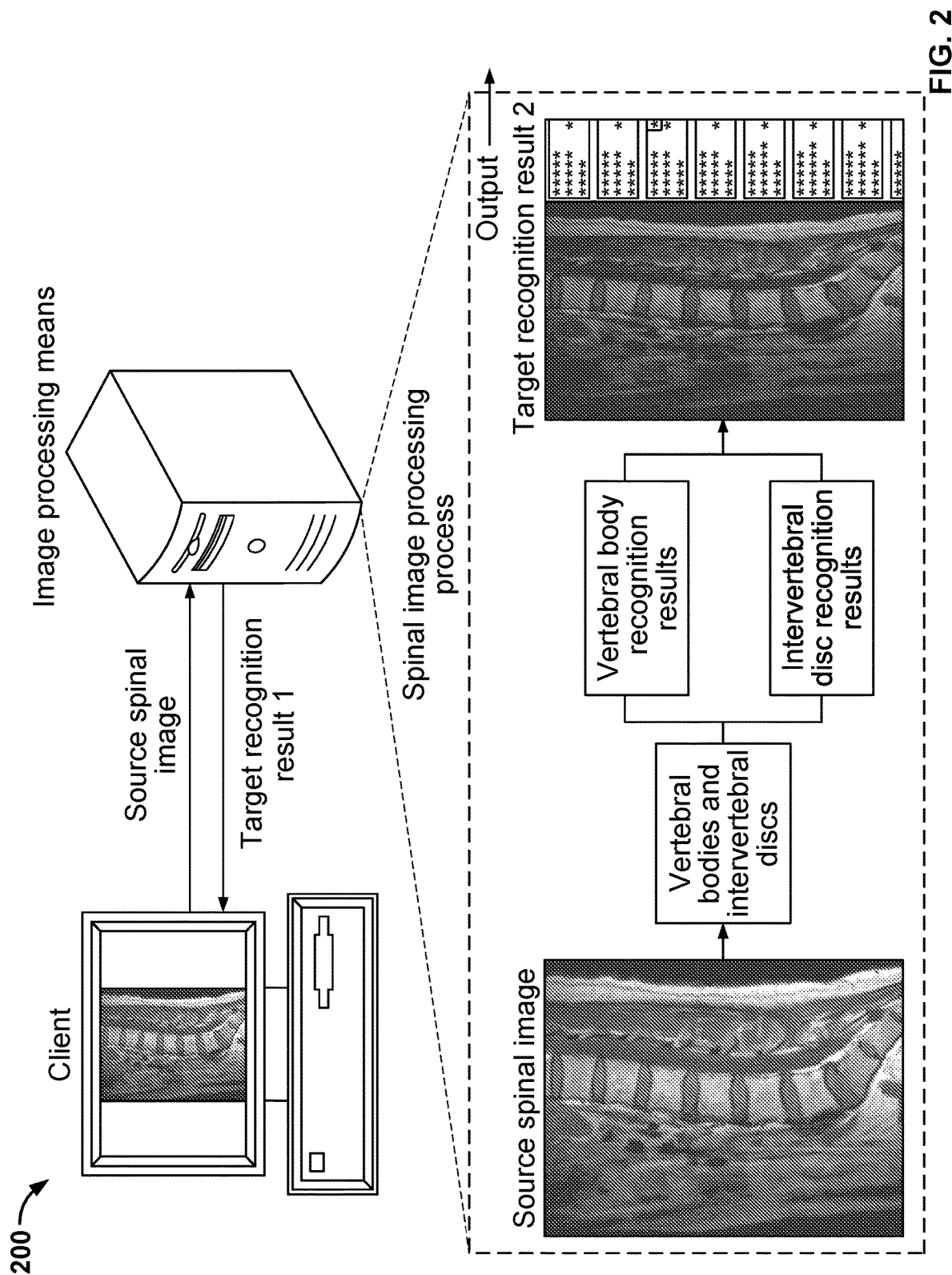
FIG. 2 is diagram of an application of a method for processing a spinal image according to various embodiments of the present application.

FIG. 2 is diagram of an application of a method for processing a spinal image according to various embodiments of the present application.

Referring to FIG. 2, system 200 may implement a method for processing a source spinal image. In some embodiments, system 200 implements process 100 of FIG. 1. System 200 may include a client terminal and an image processing means (e.g., a server or other terminal) connected to the client terminal such as via one or more networks.

The image processing means may obtain a source spinal image. In some embodiments, the image processing means receives the source spinal image from the client terminal. For example, the client terminal may send the source spinal image to the image processing means. As another example, the client terminal may send information pertaining to a user selection of a source spinal image to the image processing means.

In response to obtaining the source spinal image, the image processing means may process the source spinal image to determine a target recognition result. According to various embodiments, in response to determining the target recognition result, the image processing mean may send the target recognition result to the client terminal (or an indication that the target recognition result are available for viewing). The image processing means may process the source spinal image to determine one or more vertebral bodies and/or one or more intervertebral discs. In response to determining the one or more vertebral bodies and/or one or more intervertebral discs, the image processing means may determine one or more vertebral body recognition results and/or one or more intervertebral disc recognition results. In response to determining the one or more vertebral body recognition results and/or one or more intervertebral disc recognition results, the image processing means may determine the target recognition results (e.g., based at least in part on the one or more vertebral body recognition results and/or one or more intervertebral disc recognition results).

Figure 4:
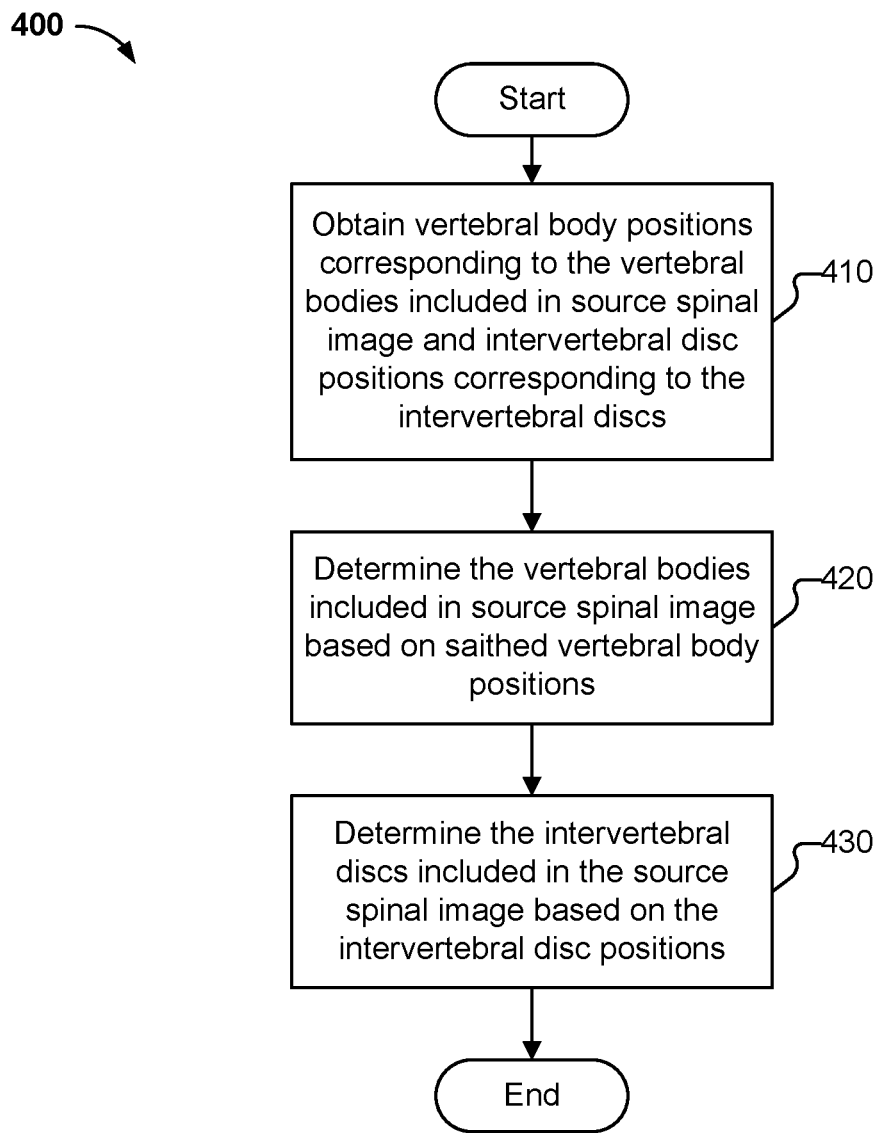
FIG. 4 is a flow diagram of a method for recognizing vertebral bodies and intervertebral discs included in a spinal image according to various embodiments of the present application.

FIG. 4 is a flow diagram of a method for recognizing vertebral bodies and intervertebral discs included in a spinal image according to various embodiments of the present application.

Referring to FIG. 4, process 400 may be implemented by a terminal. For example, process 400 may be implemented by an image capturing device such as a mobile phone, a tablet, etc. As another example, process 400 may be implemented in connection with medical imaging (e.g., by a terminal or server associated with processing images captured by a medical device such as an x-ray, an magnetic resonance imaging (MM), etc.). Process 400 may be implemented in connection with other imaging/image capturing technologies. Process 400 may be implemented by one or more servers that perform image processing and/or analysis with respect to one or more source images.

At 410, vertebral body positions corresponding to the vertebral bodies included in the source spinal image and intervertebral disc positions corresponding to the intervertebral discs are obtained.

In response to obtaining the source spinal image, analytical processing may be performed with respect to one or more of the pixels comprised in the source spinal image to obtain vertebral body positions corresponding to the vertebral bodies included in the source spinal image and intervertebral disc positions corresponding to intervertebral discs. In some embodiments, the vertebral body positions may be vertebral body center positions for labeling the regions in which the vertebral bodies are located, and the intervertebral disc positions may be intervertebral disc center positions for labeling the regions in which the intervertebral discs are located.

At 420, the vertebral bodies included in the source spinal image based on the vertebral body positions are determined.

After the vertebral body positions are obtained (e.g., determined), the vertebral bodies included in the source spinal image may be determined based at least in part on the vertebral body positions. In some embodiments, the determining the vertebral bodies included in the source spinal image based at least in part on the vertebral body positions may include: determining vertebral body positions as vertebral bodies included in the source spinal image; or obtaining first preset regions that include vertebral body positions and determining the first preset regions as vertebral bodies included in the source spinal image.

For example, performing analytical processing with respect to the source spinal image may facilitate/allow the system, server, or other image processing means to obtain (e.g., determine) vertebral body position P1, vertebral body position P2, and vertebral body position P3 that correspond to vertebral bodies. In some embodiments, vertebral body position P1 may be determined as Vertebral Body A, vertebral body position P2 as Vertebral Body B, and vertebral body position P3 as Vertebral Body C.

In some embodiments, after vertebral body position P1, vertebral body position P2, and vertebral body position P3 that correspond to vertebral bodies are acquired, the system, server, or other image processing means may determine region S1 in which a vertebral body corresponding to vertebral body position P1 is located, region S2 in which a vertebral body corresponding to vertebral body position P2 is located, and region S3 in which a vertebral body corresponding to vertebral body position P3 is located. Region S1 can then be determined as Vertebral Body a, region S2 as Vertebral Body b, and region S3 as Vertebral Body c.

Various embodiments described above effectively implement vertebral body position-based determination of vertebral bodies included in the source spinal image and further increase the accuracy and reliability of vertebral body determinations.

At 430, the intervertebral discs included in the source spinal image are determined based at least in part on the intervertebral disc positions.

After the intervertebral disc positions are obtained (e.g., determined), the intervertebral discs included in the source spinal image may be determined based at least in part on the intervertebral disc positions. Specifically, determining the intervertebral discs included in the source spinal image based at least in part on the intervertebral disc positions may include: determining intervertebral disc positions as intervertebral discs included in the source spinal image; or acquiring second preset regions that include intervertebral disc positions and determining the second preset regions as intervertebral discs included in the source spinal image.

For example, performing analytical processing with respect to the source spinal image may facilitate/allow the system, server, or other image processing means to obtain (e.g., determine) intervertebral disc position P'1, intervertebral disc position P'2, and intervertebral disc position P'3 that correspond to intervertebral discs. In some embodiments, intervertebral disc position P'1 may be determined as Intervertebral Disc A, intervertebral disc position P'2 as Intervertebral Disc B, and intervertebral disc position P'3 as Intervertebral Disc C.

In some embodiments, after intervertebral disc position P'1, intervertebral disc position P'2, and intervertebral disc position P'3 that correspond to intervertebral discs are obtained (e.g., determined), the system, server, or other image processing means to may obtain (e.g., determine) region S'1 in which an intervertebral disc corresponding to intervertebral disc position P'1 is located, region S'2 in which an intervertebral disc corresponding to intervertebral disc position P'2 is located, and region S'3 in which an intervertebral disc corresponding to intervertebral disc position P'3 is located. Region S'1 can then be determined as Intervertebral Disc a, region S'2 as Intervertebral Disc b, and region S'3 as Intervertebral Disc c.

According to various embodiments described above, an intervertebral disc position-based determination of intervertebral discs included in the source spinal image may be effectively implemented, and the accuracy and reliability of intervertebral disc determinations may be further increased.

Figure 5:
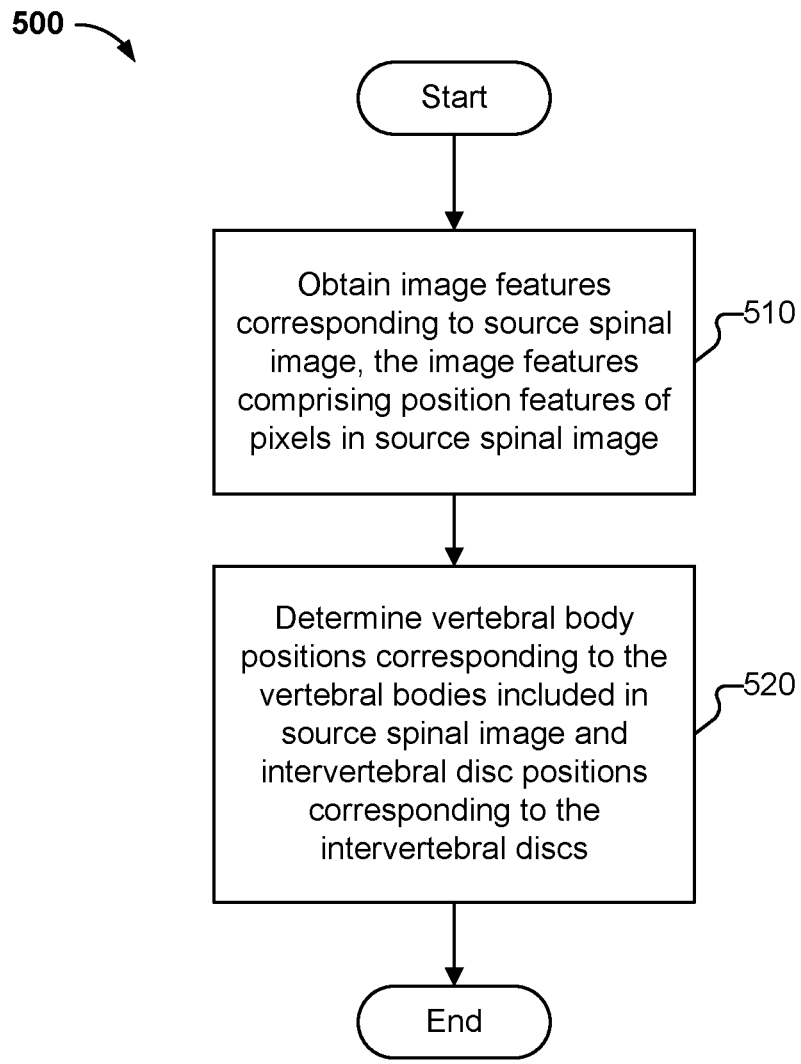
FIG. 5 is a flowchart of a method for obtaining vertebral body positions corresponding to the vertebral bodies included in a spinal image, and intervertebral disc positions corresponding to intervertebral discs according to various embodiments of the present application.

FIG. 5 is a flowchart of a method for obtaining vertebral body positions corresponding to the vertebral bodies included in a source spinal image, and intervertebral disc positions corresponding to intervertebral discs according to various embodiments of the present application.

Referring to FIG. 5, process 500 may be implemented by a terminal. For example, process 500 may be implemented by an image capturing device such as a mobile phone, a tablet, etc. As another example, process 500 may be implemented in connection with medical imaging (e.g., by a terminal or server associated with processing images captured by a medical device such as an x-ray, an magnetic resonance imaging (MM), etc.). Process 500 may be implemented in connection with other imaging/image capturing technologies. Process 500 may be implemented by one or more servers that perform image processing and/or analysis with respect to one or more source images.

According to various embodiments, vertebral body positions corresponding to the vertebral bodies included in the source spinal image and intervertebral disc positions corresponding to the intervertebral discs may be obtained. Process 500 may include obtaining vertebral body positions corresponding to the vertebral bodies included in the source spinal image and intervertebral disc positions corresponding to the intervertebral discs may include:

At 510, image features corresponding to the source spinal image may be obtained. In some embodiments, the image features may comprise position features of pixels in the source spinal image.

At 520, vertebral body positions corresponding to the vertebral bodies included in the source spinal image and intervertebral disc positions corresponding to the intervertebral discs are determined. In some embodiments, the vertebral body positions and the intervertebral disc positions are determined based at least in part on image features (e.g., of the source spinal image).

After the source spinal image is obtained, various embodiments may implement a preset feature extraction algorithm in connection with performing feature extraction operations on the source spinal image so as to obtain image features corresponding to the source spinal image. The image features may include position features of pixels in the source spinal image. After the image features are obtained, various embodiments may perform analytical processing with respect to the image features in connection with determining vertebral body positions corresponding to the vertebral bodies included in the source spinal image and intervertebral disc positions corresponding to the intervertebral discs.

According to various embodiments, determining vertebral body positions corresponding to the vertebral bodies included in the source spinal image and intervertebral disc positions corresponding to the intervertebral discs based at least in part on the image features may include: using a first convolutional neural network to perform analytical processing with respect to the image features to obtain vertebral body positions corresponding to vertebral bodies included in the source spinal image and intervertebral disc positions corresponding to the intervertebral discs. In some embodiments, the first convolutional neural network is trained for determining vertebral body positions corresponding to the vertebral bodies and/or intervertebral disc positions corresponding to the intervertebral discs in the spinal image.

Figure 6:
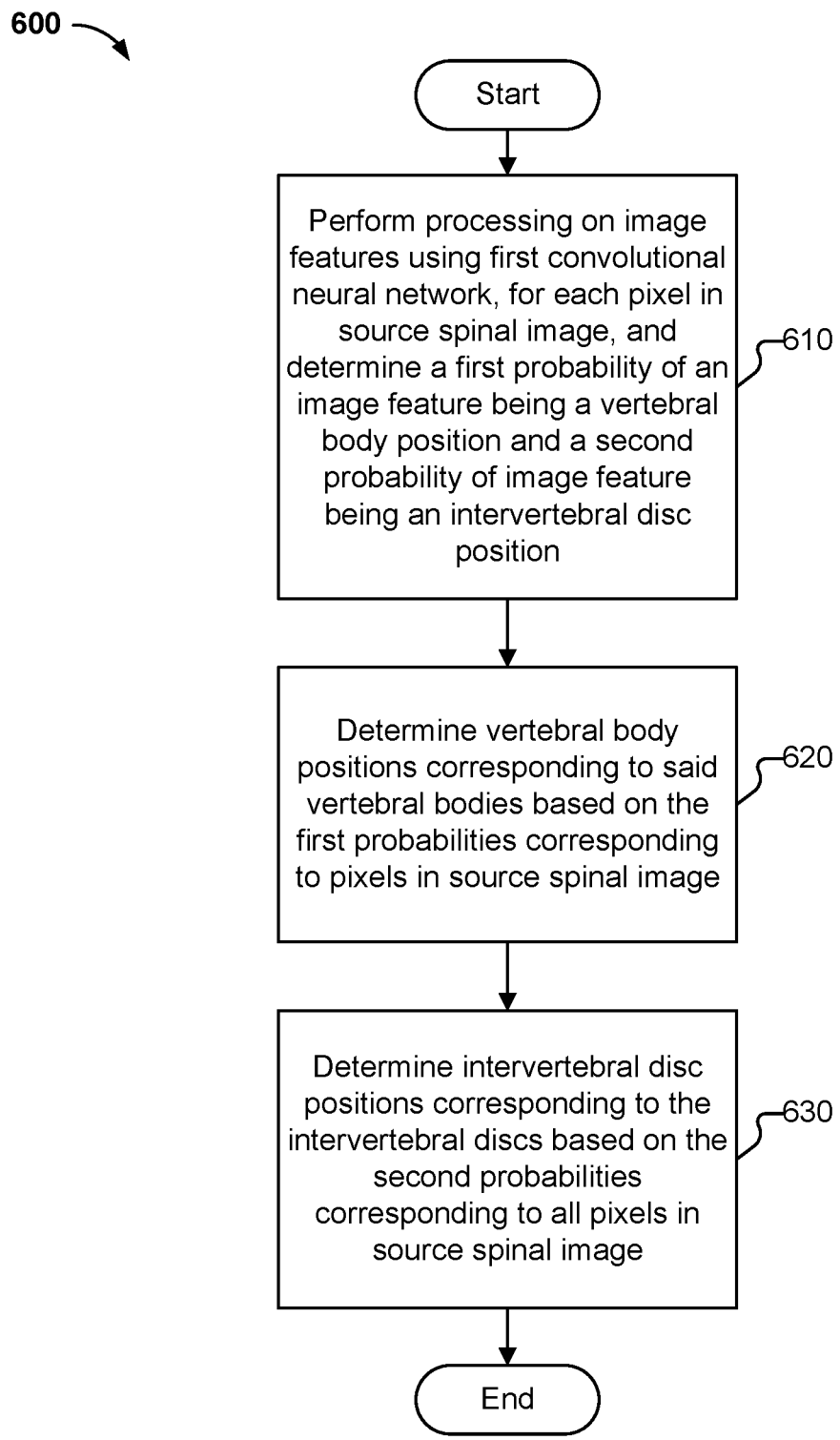
FIG. 6 is a flowchart of a method for processing a spinal image using a first convolutional neural network in connection with obtaining vertebral body positions corresponding to the vertebral bodies included in the spinal image and intervertebral disc positions corresponding to the intervertebral discs according to various embodiments of the present application.

FIG. 6 is a flowchart of a method for processing a spinal image using a first convolutional neural network in connection with obtaining vertebral body positions corresponding to the vertebral bodies included in the spinal image and intervertebral disc positions corresponding to the intervertebral discs according to various embodiments of the present application.

Referring to FIG. 6, process 600 may be implemented by a terminal. For example, process 600 may be implemented by an image capturing device such as a mobile phone, a tablet, etc. As another example, process 600 may be implemented in connection with medical imaging (e.g., by a terminal or server associated with processing images captured by a medical device such as an x-ray, an magnetic resonance imaging (MM), etc.). Process 600 may be implemented in connection with other imaging/image capturing technologies. Process 600 may be implemented by one or more servers that perform image processing and/or analysis with respect to one or more source images.

According to various embodiments, a first convolutional neural network is used in connection with performing an analytic processing with respect to the source spinal image to obtain vertebral body positions corresponding to the vertebral bodies included in the source spinal image and intervertebral disc positions corresponding to the intervertebral discs. Process 600 may be implemented in connection with using the first convolutional neural network to obtain the vertebral body positions and/or the intervertebral disc positions.

At 610, a first convolutional neural network is used in connection with performing an analytical processing with respect to the image features to analytical processing and to obtain a first probability of the image feature or processed spinal image comprising, or being, a vertebral body position and a second probability of the image feature or processed spinal image comprising, or being, an intervertebral disc position. In some embodiments, the first convolutional neural network is used in connection with performing an analytical processing with respect to the image features, and determine, for each pixel in the processed spinal image, a first probability that the pixel corresponds to a vertebral body position and/or a second probability that the pixel corresponds to an intervertebral disc position. For example, the first convolutional network may be used to determine pixel-by-pixel probabilities that a particular pixel corresponds to a vertebral body position and/or intervertebral disc position.

According to various embodiments, because the image features include position features of pixels in the source spinal image, with the use of the first convolutional neural network to perform analytical processing with respect to the image features for each pixel in the source spinal image, a first probability of the pixel being a vertebral body position and a second probability of the pixel being an intervertebral disc position may be obtained.

As an example, the pixels corresponding to the image features may include: pixel a1, pixel a2, pixel a3, and pixel a4. A first convolutional neural network is then used to subject these image features in the source spinal image to analytical processing. Thus, for each pixel, a first probability of the pixel being a vertebral body position and a second probability of the pixel being an intervertebral disc position may be determined. For example, the first probabilities corresponding to pixel a1, pixel a2, pixel a3, and pixel a4 are p1, p2, p3, and p4, respectively; the second probabilities corresponding to pixel a1, pixel a2, pixel a3, and pixel a4 are p11, p12, p13, and p14, respectively.

At 620, vertebral body positions corresponding to the vertebral bodies is determined based at least in part on the first probabilities corresponding to a set of pixel points in the source spinal image. In some embodiments, the vertebral body positions corresponding to the vertebral bodies is determined based at least in part on the first probabilities corresponding to all pixel points in the source spinal image.

After the first probabilities corresponding to all pixels in the source spinal image are acquired, analytical processing may be performed with respect to the first probabilities corresponding to a set of pixels (e.g., all pixels) in the source spinal image in connection with determining the vertebral body positions corresponding to the vertebral bodies. In some embodiments, determining the vertebral body positions corresponding to the vertebral bodies based at least in part on the first probabilities corresponding to the set of pixels (e.g., all pixels) in the source spinal image may include: determining the position information corresponding to the pixel for which the first probability is the greatest of all the pixels (e.g., all the set of pixels or all the pixels in the source spinal image) as the vertebral body position corresponding to the vertebral body; or determining the region in which is located the pixel with the greatest first probability as the vertebral body position corresponding to the vertebral body.

Example 1: when determining vertebral body positions as vertebral bodies included in the source spinal image, the first probabilities corresponding to pixel a1, pixel a2, pixel a3, and pixel a4 are p1, p2, p3, and p4, respectively. These first probabilities p1, p2, p3, and p4 may be analyzed and compared. If we assume that the greatest first probability that was acquired is p2, the position information for the pixel point a2 corresponding to the first probability p2 may then be determined as the vertebral body position corresponding to the vertebral body, thus effectively ensuring that the vertebral body position is determined in an accurate and reliable manner.

Example 2: When determining a first preset region including said vertebral body position as the vertebral body included in the source spinal image, let us assume that the first preset regions include preset region a11, preset region a12, preset region a13, and preset region a14. The first probabilities corresponding to preset region a11, preset region a12, preset region a13, and preset region a14 are p11, p12, p13, and p14, respectively. These first probabilities p11, p12, p13, and p14 may be analyzed and compared. If we assume that the greatest first probability that was acquired is p12, the position information for the preset region a12 corresponding to the first probability p12 may then be determined as the vertebral body position corresponding to the vertebral body, thus effectively ensuring that the vertebral body position is determined in an accurate and reliable manner.

At 630, intervertebral disc positions corresponding to the intervertebral discs based at least in part on the second probabilities corresponding to a set of pixels in the source spinal image is determined. In some embodiments, the intervertebral disc positions corresponding to the intervertebral discs is determined based at least in part on the second probabilities corresponding to all pixel points in the source spinal image After the second probabilities corresponding to all pixels in the source spinal image are acquired, analytical processing may be performed with respect to the second probabilities corresponding to the set of pixels (e.g., all pixels) in the source spinal image in connection with determining the intervertebral disc positions corresponding to the intervertebral discs. In some embodiments, determining the intervertebral disc positions corresponding to the intervertebral discs based at least in part on the second probabilities corresponding to the set of pixels (e.g., all pixels) in the source spinal image may include: determining the position information corresponding to the pixel for which the second probability is the greatest of all the pixels (e.g., all the set of pixels or all the pixels in the source spinal image) as the intervertebral disc position corresponding to the intervertebral disc; or determining the region in which is located the pixel with the greatest second probability as the intervertebral disc position corresponding to the intervertebral disc. Please note that the intervertebral disc position and the aforementioned vertebral body position are different positions.

Example 1: when determining intervertebral disc positions as intervertebral discs included in the source spinal image, the second probabilities corresponding to pixel b1, pixel b2, pixel b3, and pixel b4 are p21, p22, p23, and p24, respectively. These second probabilities p21, p22, p23, and p24 may be analyzed and compared. If we assume that the greatest second probability that was acquired is p23, the position information for the pixel b3 corresponding to the second probability p23 may then be determined as the intervertebral disc position corresponding to the intervertebral disc, thus effectively ensuring that the intervertebral disc position is determined in an accurate and reliable manner.

Example 2: When determining a second preset region including said intervertebral disc position as the intervertebral disc included in the source spinal image, let us assume that the second preset regions include preset region b11, preset region b12, preset region b13, and preset region b14. The second probabilities corresponding to preset region b11, preset region b12, preset region b13, and preset region b14 are p31, p32, p33, and p34, respectively. These second probabilities p31, p32, p33, and p34 may be analyzed and compared. If we assume that the greatest second probability that was acquired is p34, the position information for the preset region b14 corresponding to the second probability P34 may then be determined as the intervertebral disc position corresponding to the intervertebral disc, thus effectively ensuring that the intervertebral disc position is determined in an accurate and reliable manner.

In some examples, when the image features further comprise pathologic type features corresponding to pixels in the source spinal image, various embodiments provide a specific form of implementation for determining vertebral body recognition results corresponding to the vertebral bodies and intervertebral disc recognition results corresponding to the intervertebral discs. Specifically, determining vertebral body recognition results corresponding to the vertebral bodies and intervertebral disc recognition results corresponding to the intervertebral discs may include: using a second convolutional neural network to perform analytical processing with respect to (e.g., on) the image features to obtain vertebral body recognition results corresponding to the vertebral bodies and intervertebral disc recognition results corresponding to the intervertebral discs. In some embodiments, the second convolutional neural network is trained for determining vertebral body recognition results corresponding to the vertebral bodies and intervertebral disc recognition results corresponding to the intervertebral discs in the spinal image.

Figure 7:
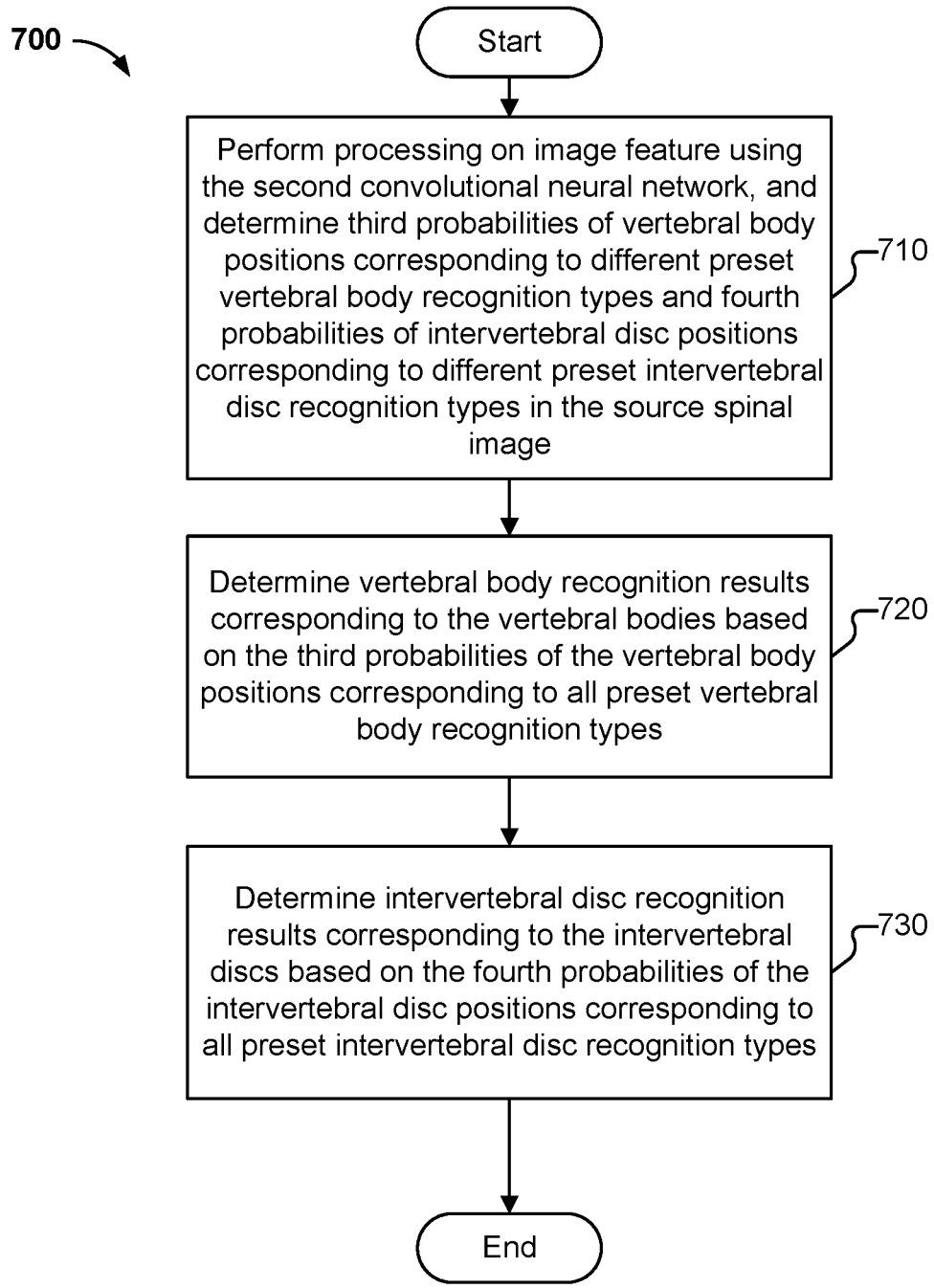
FIG. 7 is a flowchart of a method for processing a spinal image using a second convolutional neural network in connection with obtaining vertebral body recognition results corresponding to the vertebral bodies and intervertebral disc recognition results corresponding to the intervertebral discs according to various embodiments of the present application.

FIG. 7 is a flowchart of a method for processing a spinal image using a second convolutional neural network in connection with obtaining vertebral body recognition results corresponding to the vertebral bodies and intervertebral disc recognition results corresponding to the intervertebral discs according to various embodiments of the present application.

Referring to FIG. 7, process 700 may be implemented by a terminal. For example, process 700 may be implemented by an image capturing device such as a mobile phone, a tablet, etc. As another example, process 700 may be implemented in connection with medical imaging (e.g., by a terminal or server associated with processing images captured by a medical device such as an x-ray, an magnetic resonance imaging (MM), etc.). Process 700 may be implemented in connection with other imaging/image capturing technologies. Process 700 may be implemented by one or more servers that perform image processing and/or analysis with respect to one or more source images.

According to various embodiments, a second convolutional neural network is used in connection with performing an analytic processing with respect to the image features to obtain vertebral body recognition results corresponding to the vertebral bodies and intervertebral disc recognition results corresponding to the intervertebral discs. Process 700 may be implemented in connection with using the second convolutional neural network to obtain the vertebral body recognition results and/or the intervertebral disc recognition results.

At 710, a second convolutional neural network is used in connection with performing an analytical processing with respect to image features to obtain third probabilities of vertebral body positions corresponding to different preset vertebral body recognition types and fourth probabilities of intervertebral disc positions corresponding to different preset intervertebral disc recognition types in the source spinal image.

According to various embodiments, because the image features further comprise pathologic type features corresponding to pixels in the source spinal image, with the use of the second convolutional neural network to perform analytical processing with respect to the image features, third probabilities of vertebral body positions corresponding to different preset vertebral body recognition types and fourth probabilities of intervertebral disc positions corresponding to different preset intervertebral disc recognition types in the source spinal image may be obtained.

In some examples, when the vertebral bodies include lumbar vertebral bodies, the preset vertebral body recognition types include at least one of the following: normal vertebral body and vertebral body with degenerative change; and the preset intervertebral disc recognition types include at least one of the following: normal intervertebral disc and pathologic change of intervertebral disc. In some embodiments, the pathologic change of intervertebral disc comprises at least one of the following: intervertebral disc bulge and intervertebral disc herniation; intervertebral disc bulge comprises at least one of the following: diffuse intervertebral disc bulge and asymmetric intervertebral disc bulge; intervertebral disc herniation comprises at least one of the following: intervertebral disc protrusion, intervertebral disc extrusion, intervertebral disc sequestration, and intervertebral herniation.

Example 1: When determining said vertebral body position to be a vertebral body included in the source spinal image, the preset vertebral body recognition types may include: type a1, type a2, type a3, and type a4; the preset intervertebral disc recognition types may include: type b1, type b2, type b3, and type b4. Then the second convolutional neural network may be used to perform analytical processing with respect to (e.g., on) the image features. According to various embodiments, third probabilities of vertebral body positions corresponding to different preset vertebral body recognition types and fourth probabilities of intervertebral disc positions corresponding to different preset intervertebral disc recognition types in the source spinal image may be obtained. For example, the third probabilities corresponding to type a1, type a2, type a3, and type a4 are pa1, pa2, pa3, and pa4, respectively; the fourth probabilities corresponding to type b1, type b2, type b3, and type b4 are pb1, pb2, pb3, and pb4, respectively.

Example 2: When determining first preset regions including the vertebral body positions as vertebral bodies included in the source spinal image and determining second preset regions including the intervertebral disc positions as intervertebral discs included in the source spinal image, the preset vertebral body recognition types may include: type a1, type a2, type a3, and type a4; the preset intervertebral disc recognition types may include: type b1, type b2, type b3, and type b4. Then the second convolutional neural network may be used to perform analytical processing with respect to (e.g., on) the image features to analytical processing. According to various embodiments, third probabilities of vertebral body positions corresponding to different preset vertebral body recognition types and fourth probabilities of intervertebral disc positions corresponding to different preset intervertebral disc recognition types in different first preset regions and different second preset regions of the source spinal image.

According to various embodiments, because a first preset region may include multiple pixels and a second preset region may include multiple pixels, a second convolutional network may be used to perform analytical processing with respect to the image features to obtain (e.g., determine) third probabilities of different pixels corresponding to different preset vertebral body recognition types in the first preset region and fourth probabilities of different pixels corresponding to different preset intervertebral disc recognition types in the second preset region, as shown in the table below:

|                    | Pixel a1 | Pixel a2 | Pixel a3 |
|--------------------|----------|----------|----------|
| Recognition type 1 | p11      | p21      | p31      |
| Recognition type 2 | p12      | p22      | p32      |
| Recognition type 3 | p13      | p23      | p33      |

In the table, the probability p11 (which may be a third probability or a fourth probability) may be used to denote the probability information of pixel a1 corresponding to recognition type 1, the probability p21 may be used to denote the probability information of pixel a2 corresponding to recognition type 1, and the probability p31 may be used to denote the probability information of pixel a3 corresponding to recognition type 1. The content expressed by the other probabilities (probabilities p21, p22, p23, p31, p32, and p33) is similar to the probability information described above and will not be discussed further here.

At 720, vertebral body recognition results corresponding to the vertebral bodies based on the third probabilities of the vertebral body positions corresponding to a set of preset vertebral body recognition types is determined. In some embodiments, the vertebral body recognition results corresponding to the vertebral bodies based on the third probabilities of the vertebral body positions corresponding to all of the preset vertebral body recognition types is determined.

After the third probabilities of vertebral body positions corresponding to a set of preset vertebral body recognition types are obtained (e.g., after probabilities of vertebral body positions corresponding to all of the set of the preset vertebral body recognition types are obtained), analytical processing may be performed with respect to the third probabilities of the vertebral body positions corresponding to the set of preset vertebral body recognition types (e.g., all of the set) to determine vertebral body recognition results corresponding to the vertebral bodies. In some embodiments, the determining vertebral body recognition results corresponding to the vertebral bodies based on the third probabilities of the vertebral body positions corresponding to the set of preset vertebral body recognition types may include: determining the preset vertebral body recognition type for which the third probability is the greatest of all of the set of preset vertebral body recognition types as the vertebral body recognition result corresponding to the vertebral body.

For example, when the third probabilities corresponding to type a1, type a2, type a3, and type a4 are pa1, pa2, pa3, and pa4, respectively, these third probabilities pa1, pa2, pa3, and pa4 may be analyzed and compared. If we assume that the greatest third probability that was acquired is pa4, type a4 corresponding to the third probability Pa4 may then be determined as the vertebral body recognition result corresponding to the vertebral body, thus effectively ensuring that the vertebral body recognition result is determined in an accurate and reliable manner.

At 730, intervertebral disc recognition results corresponding to the intervertebral discs based at least in part on the fourth probabilities of the intervertebral disc positions corresponding to a set of preset intervertebral disc recognition types is determined. In some embodiments, the intervertebral disc recognition results based at least in part on the fourth probabilities of the intervertebral disc positions for all the set of preset intervertebral disc recognition types is determined.

After the fourth probabilities of intervertebral disc positions corresponding to the set of (e.g., all of the set) preset intervertebral disc recognition types are obtained, analytical processing is performed with respect to the fourth probabilities of the intervertebral disc positions corresponding to the set of (e.g., of the set) preset intervertebral disc recognition types to determine intervertebral disc recognition results corresponding to the intervertebral discs. In some embodiments, the determining intervertebral disc recognition results corresponding to the intervertebral discs based at least in part on the fourth probabilities of the intervertebral disc positions corresponding to the set of preset intervertebral disc recognition types may include: determining the preset intervertebral disc recognition type for which the fourth probability is the greatest of all preset intervertebral disc recognition types as the intervertebral disc recognition result corresponding to the intervertebral disc.

For example, when the fourth probabilities corresponding to type b1, type b2, type b3, and type b4 are pb1, pb2, pb3, and pb4, respectively, these fourth probabilities pb1, pb2, pb3, and pb4 may be analyzed and compared. If we assume that the greatest fourth probability that was acquired is pb1, type b1 corresponding to the fourth probability pb1 may then be determined as the intervertebral disc recognition result corresponding to the intervertebral disc, thus effectively ensuring that the intervertebral disc recognition result is determined in an accurate and reliable manner.

Figure 8:
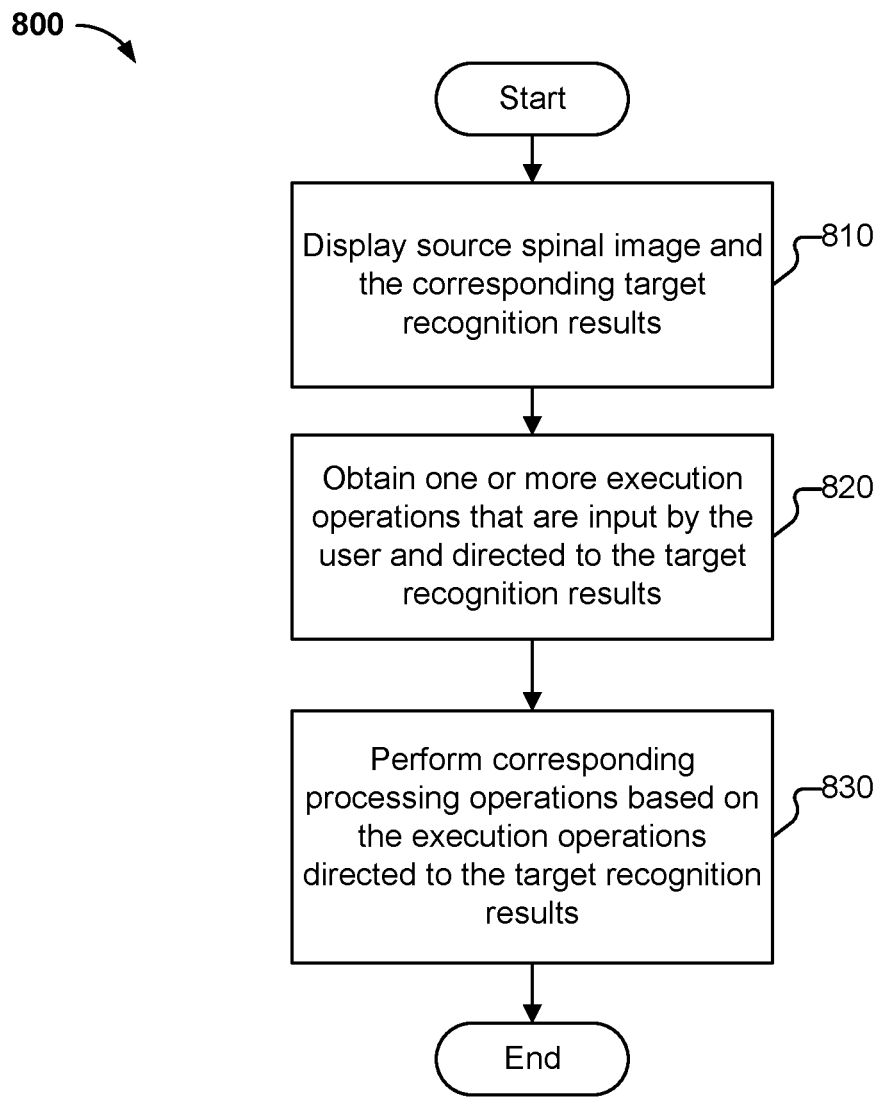
FIG. 8 is a flowchart of a method for processing a spinal image according to various embodiments of the present application.

FIG. 8 is a flowchart of a method for processing a spinal image according to various embodiments of the present application.

At 810, the source spinal image and the corresponding target recognition results are displayed. In some embodiments, the source spinal image and corresponding target recognition results are provided at the client terminal. A server may cause a user interface of the client terminal to display the source spinal image and corresponding target recognition results.

At 820, one or more execution operations that are input by the user and directed at the target recognition results are obtained. The client terminal may obtain one or more user inputs (e.g., to the user interface) directed to target recognition results. In some embodiments, in response to receiving the one or more user inputs, the client terminal may provide information pertaining to the one or more user inputs to one or more processors that perform an operation such an image analysis of the source spinal image. For example, the client terminal may send the information pertaining to the one or more user inputs to a server.

At 830, corresponding processing operations based on the execution operations directed at the target recognition results are performed. In some embodiments, the client terminal may perform the processing operations based at least in part on the one or more user inputs directed to target recognition results. In some embodiments, in response to receiving the information pertaining to the one or more inputs, a server performs one or more corresponding operations based at least in part on the one or more user inputs.

After target recognition results corresponding to the source spinal image are obtained, the source spinal image and the corresponding target recognition results may be displayed by a display device.

Figure 9:
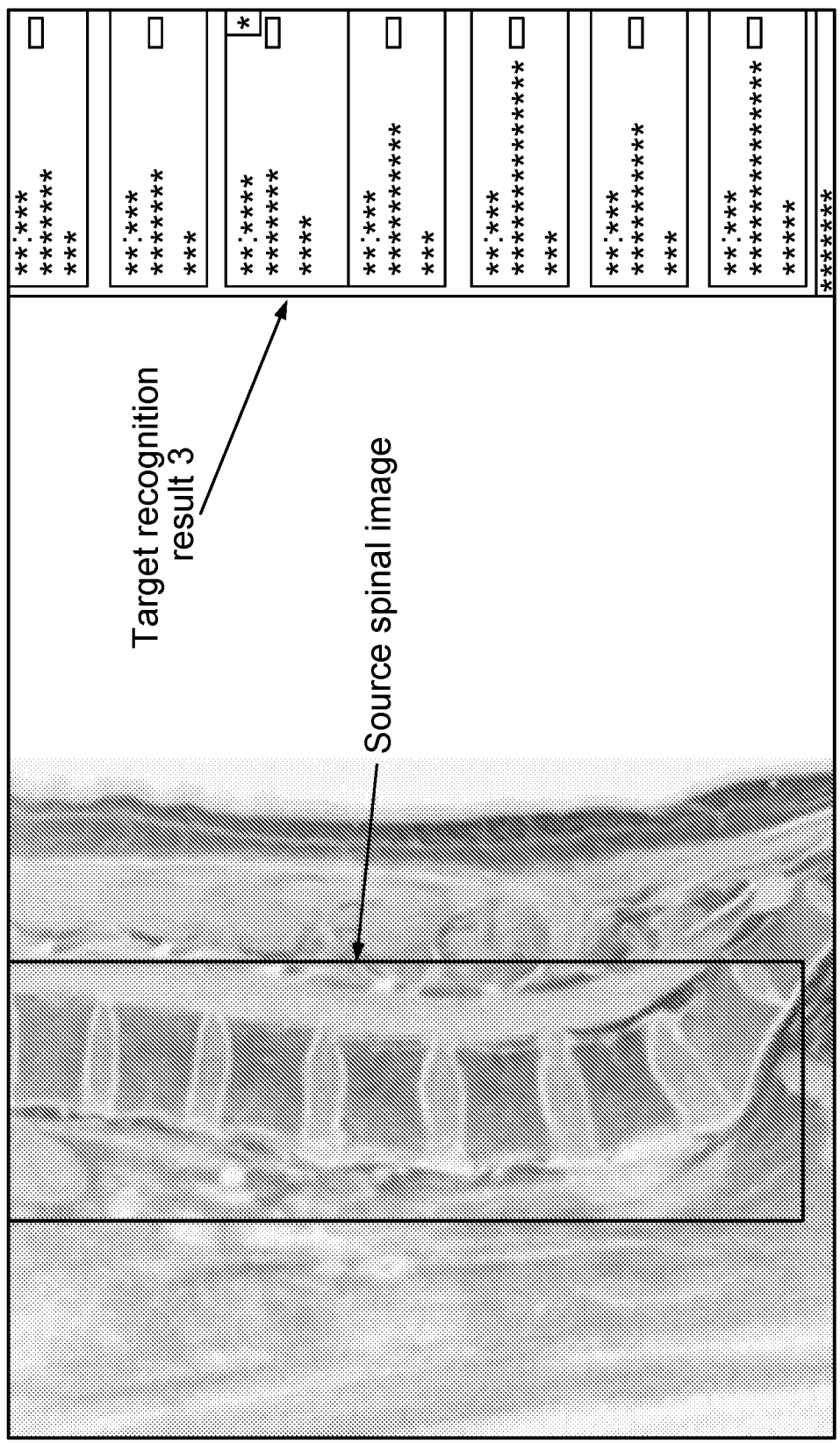
FIG. 9 is a diagram displaying a spinal image and corresponding target recognition results according to various embodiments of the present application.

FIG. 9 is a diagram displaying a spinal image and corresponding target recognition results according to various embodiments of the present application.

Referring to FIG. 9, the display of the spinal image and corresponding target recognition results may be implemented by a terminal, such as a mobile phone, a tablet, a personal computer, a TV, etc. The spinal image may be displayed at one part of an interface and the corresponding target recognition results may be displayed at another part of the user interface. As illustrated in FIG. 9, the source spinal image, which includes vertebral bodies and intervertebral discs, may be displayed in the central area of the display interface. The target recognition results corresponding to the source spinal image may be displayed on the right side of the display interface.

According to various embodiments, the spinal image and corresponding target recognition results are displayed in a manner that conveniently and effectively provides the target recognition results with an associated spinal image (or part thereof).

Figure 10:
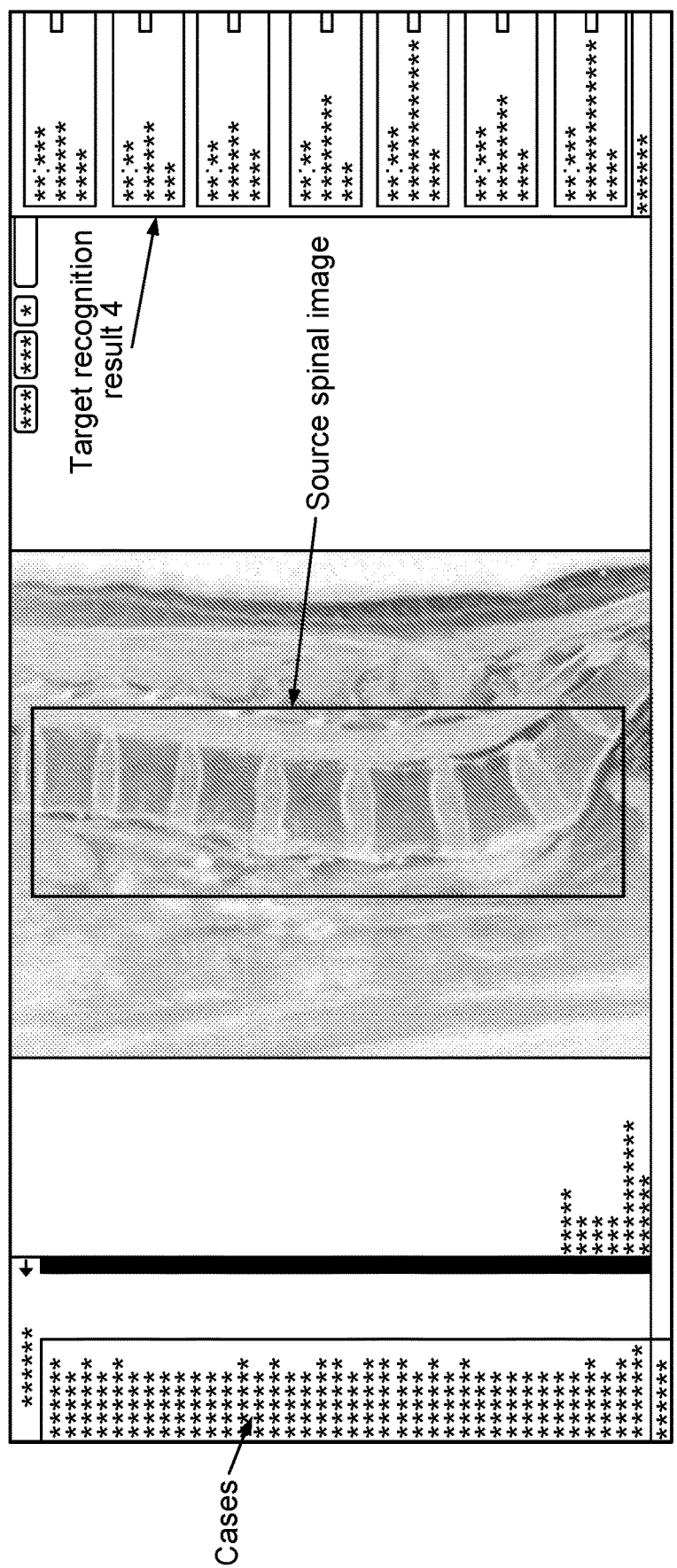
FIG. 10 is a diagram displaying a spinal image and corresponding target recognition results according to various embodiments of the present application.

FIG. 10 is a diagram displaying a spinal image and corresponding target recognition results according to various embodiments of the present application.

Referring to FIG. 10, the display of the spinal image and corresponding target recognition results may be implemented by a terminal, such as a mobile phone, a tablet, a personal computer, a TV, etc. The spinal image may be displayed at one part of an interface and the corresponding target recognition results may be displayed at another part of the user interface.

In some embodiments, additional informational is provided on the interface that provides the source spinal image and corresponding target recognition results. For example, information pertaining to a medical record corresponding to the source spinal image may be displayed. The information pertaining to the medical record may include one or more of patient information, an analysis of the source spinal image and/or target results (e.g., a medical practitioner's notes, etc.). As another example, control elements may be displayed besides or as overlaid relative to the source spinal image. The control elements may allow a user to label the source spinal image, edit the target results, confirm the target results, etc.

As illustrated in FIG. 10, case information corresponding to the source spinal image may be displayed on the left side of the display interface.

After the source spinal image and the corresponding target recognition results are displayed, the user may input appropriate operations in relation to the vertebral bodies, intervertebral discs, and target recognition results displayed on the display interface. When the user inputs an execution operation directed at a target recognition result, the execution operation that is input by the user and directed at the target recognition result may be obtained. For example, when a click or touch operation executed by the user on a vertebral body in the source spinal image is obtained, the corresponding vertebral body recognition result is highlighted in the target recognition results display area on the display interface. When the user inputs a viewing operation directed at a target recognition result, detailed information about the corresponding target recognition result may be provided to the user. When an editing operation that is input by the user and directed at a target recognition result is obtained, the editing operation may serve as a basis for the user to perform an editing operation, such as add, delete, revise, or mark, on the target recognition result.

In some embodiments, the source spinal image and the corresponding target recognition results are displayed, an execution operation that is input by the user and directed at a target recognition result is obtained, and an appropriate processing operation is performed on the target recognition result based on the execution operation. In this way, interactive operations with the user are effectively implemented, with the result that the user can, as necessary or as requested/desired, perform appropriate editing operations on the target recognition results, thus further expanding the utility of various embodiments and improving the flexibility and reliability with which various embodiments are used, while ensuring a good user experience.

Figure 11:
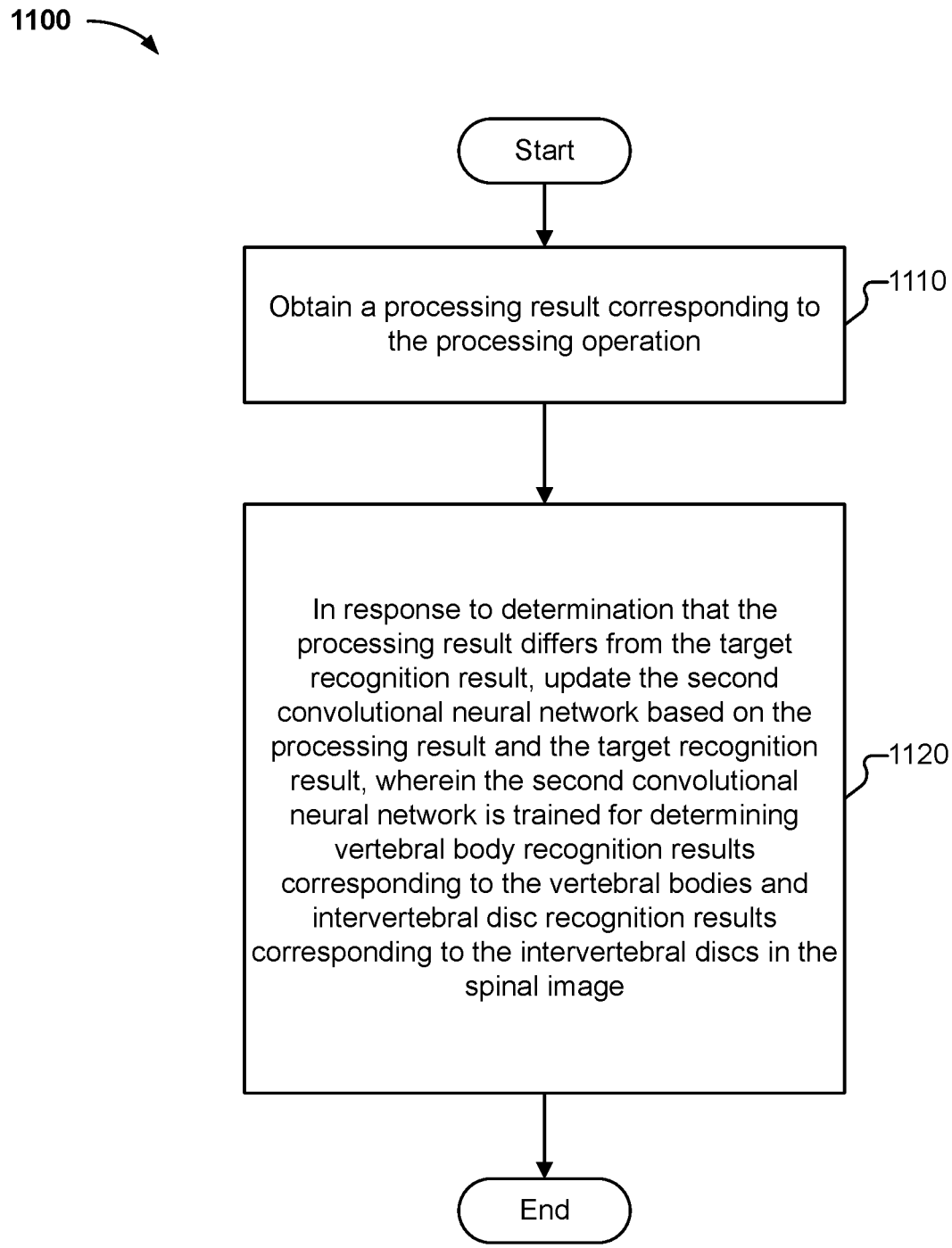
FIG. 11 is a flowchart of a method for processing a spinal image according to various embodiments of the present application.

FIG. 11 is a flowchart of a method for processing a spinal image according to various embodiments of the present application.

Referring to FIG. 11, process 1100 may be implemented by a terminal. For example, process 1100 may be implemented by an image capturing device such as a mobile phone, a tablet, etc. As another example, process 1100 may be implemented in connection with medical imaging (e.g., by a terminal or server associated with processing images captured by a medical device such as an x-ray, an magnetic resonance imaging (MM), etc.). Process 1100 may be implemented in connection with other imaging/image capturing technologies. Process 1100 may be implemented by one or more servers that perform image processing and/or analysis with respect to one or more source images. According to various embodiments, process 1100 is performed in response to a user input with respect to the source spinal image or corresponding target recognition results. For example, a terminal or server implements process 1100 based at least in part on a user input with respect to an execution operation.

At 1110, a processing result corresponding to the processing operation is obtained.

At 1120, in response to a determination that the processing result differs from the target recognition result, the second convolutional neural network is updated based at least in part on the processing result and the target recognition result. The second convolutional neural network may be trained for determining vertebral body recognition results corresponding to the vertebral bodies and intervertebral disc recognition results corresponding to the intervertebral discs in the source spinal image. The vertebral body recognition results and the intervertebral disc recognition results may be related to the target recognition results.

After an execution operation that is input by the user and directed at a target recognition result is obtained, a processing operation on the target recognition result may be performed based at least in part on the execution operation, and a processing result corresponding to the processing operation may be obtained. After the processing operation is obtained, the processing result and the target recognition result may be analyzed and compared. A determination that the processing result differs from the target recognition result may correspond to the user performing an editing operation on a target recognition result that was obtained in advance. For example, the user performed a revision or deletion operation on a description error or a deviation in the target recognition result. At this point, the corresponding processing result after the editing operation differs from the target recognition result. The second convolutional neural network can then be updated based on the processing result and the target recognition result. In some embodiments, the second convolutional neural network is trained for determining vertebral body recognition results corresponding to the vertebral bodies and intervertebral disc recognition results corresponding to the intervertebral discs in the spinal image. The vertebral body recognition results and the intervertebral disc recognition results may be related to the target recognition results. Performing an update operation on the second convolutional neural network can improve accuracy the next time the second convolutional network is used to subject the spinal image to analytical processing.

Figure 12:
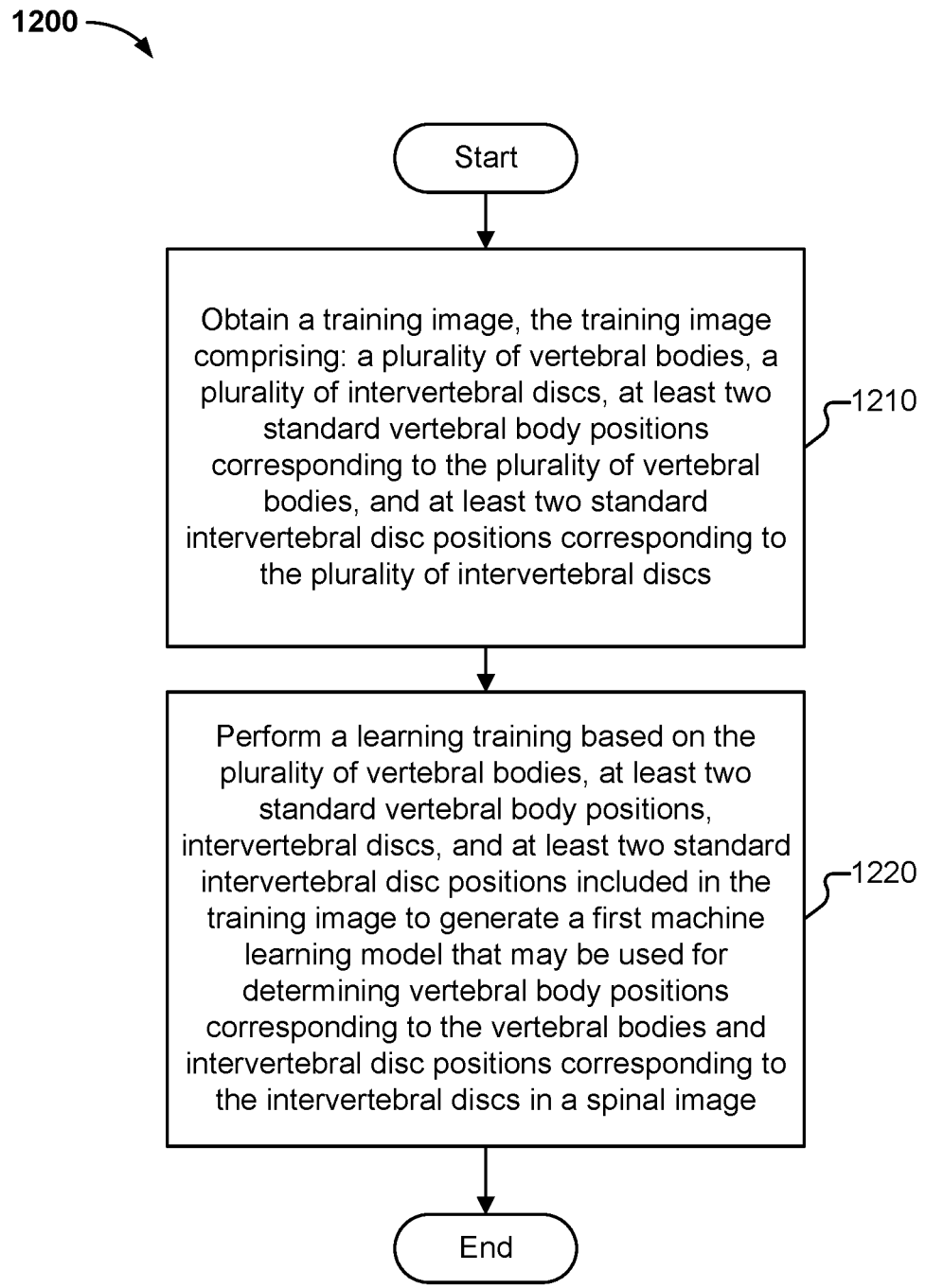
FIG. 12 is a flowchart of a method for processing a training model according to various embodiments of the present application.

FIG. 12 is a flowchart of a method for processing a training model according to various embodiments of the present application.

Referring to FIG. 12, process 1200 may be implemented by a terminal. For example, process 1200 may be implemented by an image capturing device such as a mobile phone, a tablet, etc. As another example, process 1200 may be implemented in connection with medical imaging (e.g., by a terminal or server associated with processing images captured by a medical device such as an x-ray, an magnetic resonance imaging (MM), etc.). Process 1200 may be implemented in connection with other imaging/image capturing technologies. Process 1200 may be implemented by one or more servers that perform image processing and/or analysis with respect to one or more source images. According to various embodiments, process 1200 is performed in response to a user input with respect to the source spinal image or corresponding target recognition results. For example, a terminal or server implements process 1200 based at least in part on a user input with respect to an execution operation.

According to various embodiments, process 1200 is implemented by a model training means such as one or more servers. The model training means may be understood as being implemented as software or as a combination of software and hardware.

At 1210, a training image is obtained. The training image comprising vertebral bodies, intervertebral discs, at least two standard vertebral body positions corresponding to the vertebral bodies, and at least two standard intervertebral disc positions corresponding to the intervertebral discs. In some embodiments, the obtaining the training image includes receiving an image selected by a user. In some embodiments, the obtaining the training image includes receiving a current image from a set of training images as the model is iteratively trained.

The "training image" refers to one or more standard spinal images used for learning training. The standard spinal image may include vertebral bodies, intervertebral discs, at least two standard vertebral body positions corresponding to the vertebral bodies, and at least two standard intervertebral disc positions corresponding to the intervertebral discs. The standard vertebral body positions and standard intervertebral disc positions may be positions labeled by the user as meeting preset requirements.

In some examples, to be able to ensure the quality and efficiency of learning training by a first machine learning model, at least two standard vertebral body positions in the training image conform to a Gaussian distribution. In the training image, at least two standard intervertebral disc positions conform to a Gaussian distribution.

According to various embodiments, various training models or methods for training a model based at least in part an obtained training image may be implemented. For example, the training image may be directly uploaded by the user to a model training means, thus enabling the model training means to acquire the training image in a stable manner. As another example, the training image may be stored in a preset area such as a database of training images or samples images, etc. The training model means may acquire the training image by accessing the preset area.

At 1220, a learning training is performed based at least in part on the vertebral bodies, at least two standard vertebral body positions, intervertebral discs, and at least two standard intervertebral disc positions included in the training image to generate a first machine learning model. For example, the model may be trained to associate the various parts of the training image with the locations on the training image at which the various parts are included. The model may be trained to associate one or more characteristics with the various parts of the training image (e.g., the vertebral bodies, the vertebral body positions, the standard intervertebral disc positions, and/or the standard intervertebral disc positions). The first machine learning model may be used in connection with determining vertebral body positions corresponding to the vertebral bodies and intervertebral disc positions corresponding to the intervertebral discs in a spinal image.

After the training image is acquired, the vertebral bodies, at least two standard vertebral body positions, intervertebral discs, and at least two standard intervertebral disc positions included in the training image may serve as a basis to conduct learning training. In some embodiments, the vertebral bodies, at least two standard vertebral body positions, intervertebral discs, and at least two standard intervertebral disc positions may be input into a classifier for learning training and for performing computations using a cross entropy loss function so as to obtain loss values for model learning training. The training parameters of the model are then updated based on the obtained loss values until the obtained loss values meet preset requirements. It is thereupon possible to obtain a first machine learning model for determining vertebral body positions corresponding to vertebral bodies and intervertebral disc positions corresponding to intervertebral discs in a spinal image. After the first machine learning model is obtained, the first machine learning model may be used to perform recognition operations for vertebral body positions and intervertebral disc positions on a set of source spinal images.

A model training method provided by various embodiments includes obtaining a training image, and using the vertebral bodies, at least two standard vertebral body positions (e.g., normal positions, positions according to a healthy spine, etc.), intervertebral discs, and at least two standard intervertebral disc positions (e.g., normal positions, positions according to a healthy spine, etc.) included in the training image as a basis to conduct learning training to generate a first machine learning model. The use of the vertebral bodies, normal vertebral body positions, intervertebral discs, and normal intervertebral disc positions not only ensures the quality and efficiency of the learning training of the first machine learning model, but also enables the first machine learning model to be used as a basis to achieve quick and accurate recognition operations for vertebral body positions and intervertebral disc positions on a set of source spinal images. Further, the accuracy and reliability of applications performed by the first machine learning model is improved.

Figure 13:
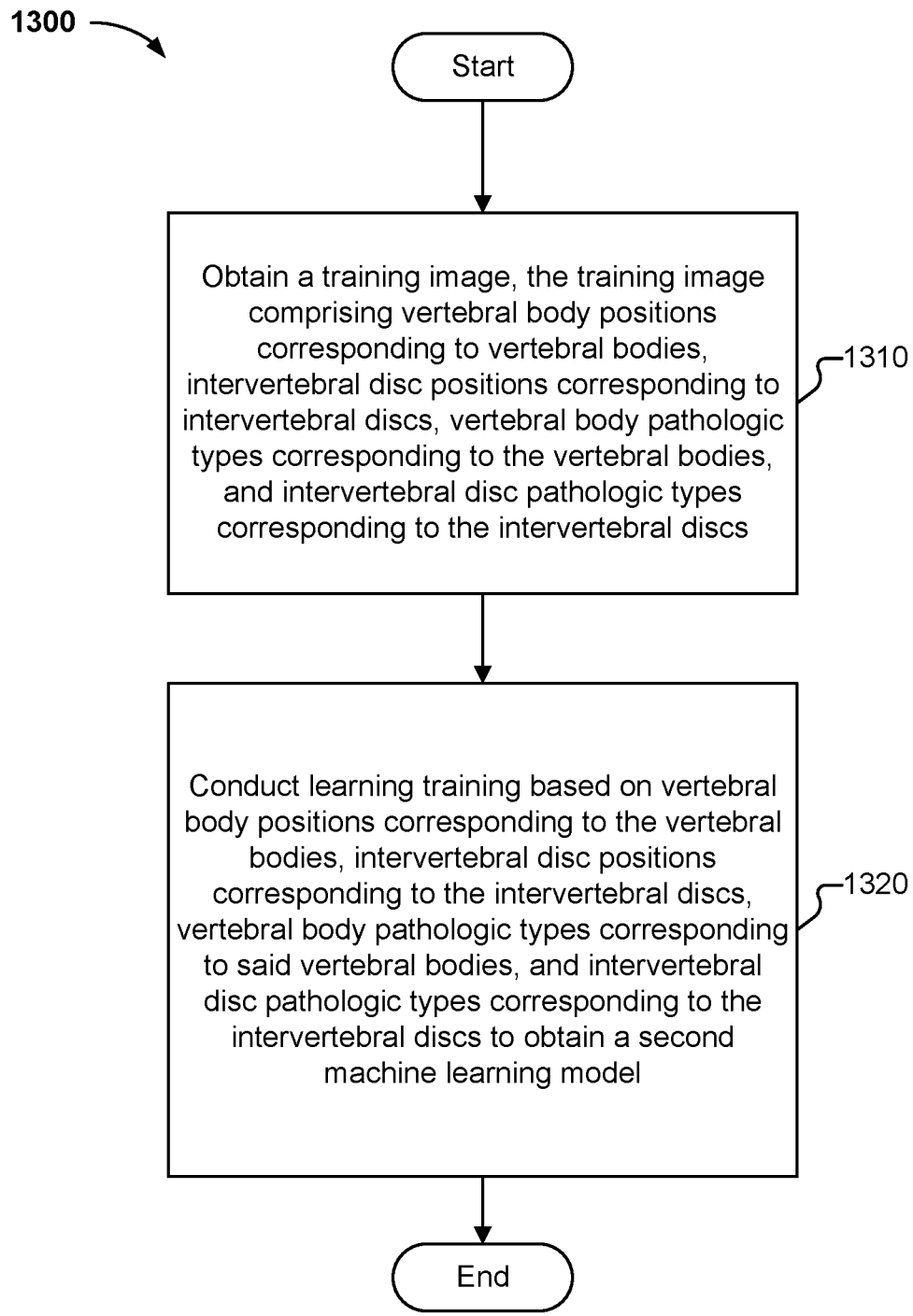
FIG. 13 is a flowchart of a method for processing a training model according to various embodiments of the present application.

FIG. 13 is a flowchart of a method for processing a training model according to various embodiments of the present application.

Referring to FIG. 13, process 1300 may be implemented by a terminal. For example, process 1300 may be implemented by an image capturing device such as a mobile phone, a tablet, etc. As another example, process 1300 may be implemented in connection with medical imaging (e.g., by a terminal or server associated with processing images captured by a medical device such as an x-ray, an magnetic resonance imaging (MM), etc.). Process 1300 may be implemented in connection with other imaging/image capturing technologies. Process 1300 may be implemented by one or more servers that perform image processing and/or analysis with respect to one or more source images. According to various embodiments, process 1300 is performed in response to a user input with respect to the source spinal image or corresponding target recognition results. For example, a terminal or server implements process 1300 based at least in part on a user input with respect to an execution operation.

According to various embodiments, process 1300 is implemented by a model training means such as one or more servers. The model training means may be understood as being implemented as software or as a combination of software and hardware.

At 1310, a training image is obtained. The training image may comprise vertebral body positions corresponding to vertebral bodies, intervertebral disc positions corresponding to intervertebral discs, vertebral body pathologic types corresponding to the vertebral bodies, and intervertebral disc pathologic types corresponding to the intervertebral discs. In some embodiments, the obtaining the training image includes receiving an image selected by a user. In some embodiments, the obtaining the training image includes receiving a current image from a set of training images as the model is iteratively trained.

The "training image" refers to one or more standard spinal images used for learning training. The standard spinal image may include vertebral body positions corresponding to vertebral bodies, intervertebral disc positions corresponding to intervertebral discs, vertebral body pathologic types corresponding to the vertebral bodies, and intervertebral disc pathologic types corresponding to the intervertebral discs. The standard vertebral body positions and standard intervertebral disc positions may be positions labeled by the user as meeting preset requirements, and the vertebral body pathologic types and intervertebral disc pathologic types may be pathologic types labeled by the user as meeting preset requirements.

According to various embodiments, various training models or methods for training a model based at least in part an obtained training image may be implemented. For example, the training image may be directly uploaded by the user to a model training means, thus enabling the model training means to acquire the training image in a stable manner. As another example, the training image may be stored in a preset area such as a database of training images or samples images, etc. The training model means may acquire the training image by accessing the preset area.

At 1320, a learning training is performed based at least in part on vertebral body positions corresponding to the vertebral bodies, intervertebral disc positions corresponding to the intervertebral discs, vertebral body pathologic types corresponding to the vertebral bodies, and intervertebral disc pathologic types corresponding to the intervertebral discs to obtain a second machine learning model. For example, the model may be trained to associate the various parts of the training image with the locations on the training image at which the various parts are included. The model may be trained to associate one or more characteristics of a pathology with the various parts of the training image (e.g., the vertebral bodies, the vertebral body positions, the intervertebral disc positions, and/or the intervertebral disc positions). The second machine learning model may be used in connection with determining vertebral body recognition results corresponding to the vertebral bodies and intervertebral disc recognition results corresponding to the intervertebral discs in a spinal image.

After the training image is acquired, vertebral body positions corresponding to the vertebral bodies, intervertebral disc positions corresponding to the intervertebral discs, vertebral body pathologic types corresponding to the vertebral bodies, and intervertebral disc pathologic types corresponding to the intervertebral discs may serve as a basis for conducting learning training. In some embodiments, vertebral body positions corresponding to the vertebral bodies, intervertebral disc positions corresponding to the intervertebral discs, vertebral body pathologic types corresponding to the vertebral bodies, and intervertebral disc pathologic types corresponding to the intervertebral discs may be input into a classifier for learning training and for performing computations using a cross entropy loss function so as to obtain loss values from model learning training. The training parameters of the model are then updated based on the obtained loss values until the obtained loss values meet preset requirements. It is thereupon possible to obtain a second machine learning model for determining vertebral body pathologic types corresponding to vertebral bodies and intervertebral disc pathologic types corresponding to intervertebral discs in a spinal image. After the second machine learning model is obtained, the second machine learning model may be used to perform recognition operations for vertebral body pathologic types and intervertebral disc pathologic types on to a set of source spinal images.

A model training method provided by various embodiments includes obtaining a training image, and using vertebral body positions corresponding to the vertebral bodies, intervertebral disc positions corresponding to the intervertebral discs, vertebral body pathologic types corresponding to the vertebral bodies (e.g., an abnormal vertebral body or vertebral body position), and intervertebral disc pathologic types corresponding to the intervertebral discs (e.g., an abnormal intervertebral disc or intervertebral disc position) as a basis to conduct learning training to obtain a second machine learning model. The use of the vertebral body positions, intervertebral disc positions, vertebral body pathologic types, and intervertebral disc pathologic types not only ensures the quality and efficiency of the learning and/or training of the second machine learning model, but also enables the use of the second machine learning model as a basis to achieve quick and accurate recognition operations for vertebral body pathologic types and intervertebral disc pathologic types on set of source spinal images. Further, the accuracy and reliability of applications performed by the second machine learning model is improved.

Figure 14:
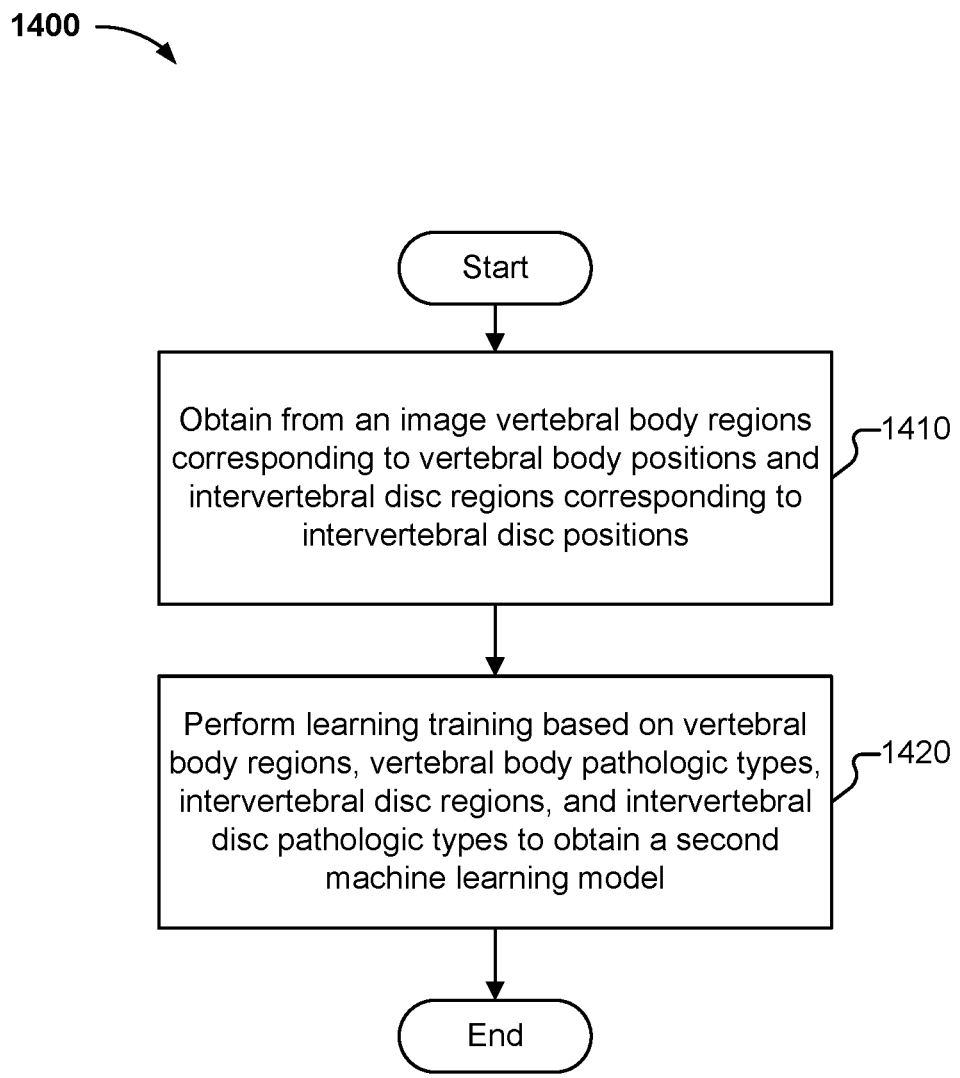
FIG. 14 is a flowchart of a method for performing learning training to obtain a second machine learning model according to various embodiments of the present application.

FIG. 14 is a flowchart of a method for performing learning training to obtain a second machine learning model according to various embodiments of the present application.

Referring to FIG. 14, process 1400 may be implemented by a terminal. For example, process 1400 may be implemented by an image capturing device such as a mobile phone, a tablet, etc. As another example, process 1400 may be implemented in connection with medical imaging (e.g., by a terminal or server associated with processing images captured by a medical device such as an x-ray, an magnetic resonance imaging (MM), etc.). Process 1400 may be implemented in connection with other imaging/image capturing technologies. Process 1400 may be implemented by one or more servers that perform image processing and/or analysis with respect to one or more source images. According to various embodiments, process 1400 is performed in response to a user input with respect to the source spinal image or corresponding target recognition results. For example, a terminal or server implements process 1400 based at least in part on a user input with respect to an execution operation.

According to various embodiments, process 1400 is implemented by a model training means such as one or more servers. The model training means may be understood as being implemented as software or as a combination of software and hardware.

At 1410, vertebral body regions corresponding to the vertebral body positions and intervertebral disc regions corresponding to the intervertebral disc positions are obtained.

According to various embodiments, the obtaining vertebral body regions corresponding to the vertebral body positions may include: obtaining a first radius for determining a vertebral body region; and determining the region within the first radius centered at the vertebral body position as the vertebral body region.

Specifically, the first radius may be a pre-assigned radius measurement for determining a corresponding vertebral body region. Various embodiments impose no restrictions as to the specific measurement magnitude of the first radius. For example, the first radius may be 3 cm, 4 cm, 5 cm, or 6 cm. The first radius may be configurable, such as by a user or an administrator based on a user preferences and/or accuracy of the diagnosis, etc.

After the vertebral body position is obtained, a first radius for determining a corresponding vertebral body region may be obtained on the basis of a preset mapping relationship between vertebral body positions and first radii. After the vertebral body position and first radius are obtained, the region within the radius centered at the vertebral body position may be determined as the vertebral body region. The vertebral body region may be a circular region or an oval region.

In some embodiments, obtaining intervertebral disc regions corresponding to the intervertebral disc positions may include: obtaining a second radius for determining an intervertebral disc region; determining the region within the second radius centered at the intervertebral disc position as the intervertebral disc region.

The second radius may be a pre-assigned radius measurement for determining a corresponding intervertebral disc region. Various embodiments impose no restrictions as to the specific measurement magnitude of the second radius. For example, the second radius may be 2.5 cm, 3 cm, 3.5 cm, 4 cm, 5 cm or 6 cm. The second radius may be configurable, such as by a user or an administrator based on a user preferences and/or accuracy of the diagnosis, etc.

After the intervertebral disc position is obtained, a second radius for determining a corresponding intervertebral disc region may be obtained on the basis of a preset mapping relationship between intervertebral disc positions and second radii. After the intervertebral disc position and second radius are obtained, the region within the radius centered at the intervertebral disc position may be determined as the intervertebral disc region. The intervertebral disc region may be a circular region or an oval region.

At 1420, the second machine learning model is obtained. In some embodiments, the second machine learning model is obtained based at least in part on performing learning training on the vertebral body regions, vertebral body pathologic types, intervertebral disc regions, and intervertebral disc pathologic types.

After acquiring vertebral body regions, vertebral body pathologic types, intervertebral disc regions, and intervertebral disc pathologic types included in the training image, the vertebral body regions, vertebral body pathologic types, intervertebral disc regions, and intervertebral disc pathologic types may be input into a classifier for learning training and for performing computations using a cross entropy loss function so as to obtain loss values for model learning training. The training parameters of the model are then updated based on the obtained loss values such as until the obtained loss values meet preset requirements. It is thereupon possible to obtain a second machine learning model for determining vertebral body pathologic types corresponding to vertebral bodies and intervertebral disc pathologic types corresponding to intervertebral discs in a spinal image. After the second machine learning model is obtained, vertebral body pathologic type and intervertebral disc pathologic type recognition operations may be performed with respect to a set of spinal images.

According to various embodiments, training a machine learning model includes obtaining vertebral body regions corresponding to vertebral body positions and intervertebral disc regions corresponding to intervertebral disc positions, and obtaining the second machine learning model based at least in part on performing a training with respect to one or more of the vertebral body regions, vertebral body pathologic types, intervertebral disc regions, and intervertebral disc pathologic types. According to various embodiments, the second machine learning model may be used in connection with analyzing and recognizing pathologic types included in preset regions. For example, the second machine learning model may be used to quickly and accurately analyze a set of source spinal images with respect to recognizing a vertebral body pathologic type and/or an intervertebral disc pathologic type. The accuracy and reliability of learning training conducted on the second machine learning model are further improved.

Figure 15:
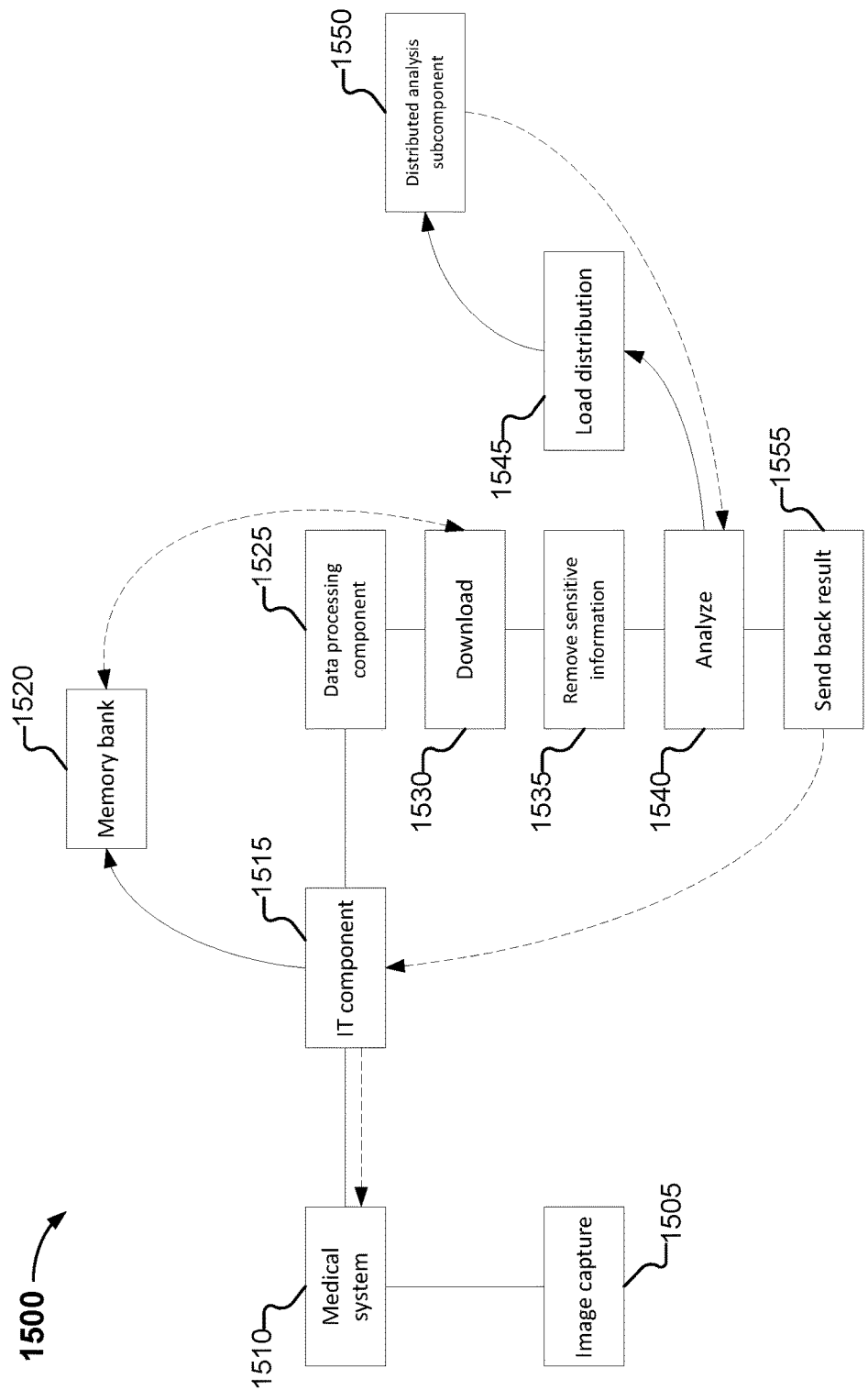
FIG. 15 is a flowchart of a method for processing a spinal image according to various embodiments of the present application.

FIG. 15 is a flowchart of a method for processing a spinal image according to various embodiments of the present application.

Referring to FIG. 15, process 1500 may be implemented by a terminal. For example, process 1500 may be implemented by an image capturing device such as a mobile phone, a tablet, etc. As another example, process 1500 may be implemented in connection with medical imaging (e.g., by a terminal or server associated with processing images captured by a medical device such as an x-ray, an magnetic resonance imaging (MM), etc.). Process 1500 may be implemented in connection with other imaging/image capturing technologies. Process 1500 may be implemented by one or more servers that perform image processing and/or analysis with respect to one or more source images. According to various embodiments, process 1500 is performed in response to a user input with respect to the source spinal image or corresponding target recognition results. For example, a terminal or server implements process 1500 based at least in part on a user input with respect to an execution operation.

According to various embodiments, process 1500 is implemented by a model training means such as one or more servers. The model training means may be understood as being implemented as software or as a combination of software and hardware.

At 1505, an image is captured. In some embodiments, an imaging system (e.g., a medical imaging device) captures a source spinal image. For example, the image may be captured in a hospital or a medical office. At 1510, a medical system may obtain the source spinal image such as in response to a user input or in connection with communicating the source spinal image.

At 1515, the source spinal image is communicated. In some embodiments, a medical system may send the captured source spinal image to an IT component so that the source spinal image may be displayed and viewed through the IT component. The source spinal image may be communicated via one or more networks.

At 1520, the source spinal image is stored in a database of source spinal images. In some embodiments, an IT component uploads the acquired source spinal image to a preset memory bank. The IT component may obtain a storage address and storage key corresponding to the source spinal image.

The preset memory bank may be a cloud memory bank or a local memory bank. For example, the preset memory bank may be an object memory bank (object storage service, OSS). In this way, the source spinal image may be uploaded and saved on the cloud. After the storage address and storage key corresponding to the source spinal image are obtained, the storage address and storage key may be sent back to the IT component to enable the IT component to obtain the storage address and storage key corresponding to the source spinal image.

At 1525, the storage address and storage key corresponding to the source spinal image are sent to the data processing component to enable the data processing component to obtain the source spinal image from the preset memory bank using the storage address and the storage key.

At 1530, the data processing component obtains the source spinal image. For example, the data processing component may download and obtain the source spinal image from the preset memory bank using the storage address and the storage key. The data processing component may be a set of one or more servers, etc.

At 1535, sensitive information is removed from the source spinal image. In some embodiments, in response to obtaining the source spinal image, processing may be performed with respect to the source spinal image to remove (e.g., delete, redact, etc.) sensitive information. For example, the user identity included in a sensitive information removal operation may be performed with respect to the source spinal image. Data leaks can thus be effectively avoided. The removal of sensitive information may further improve the security and reliability of data processing operations.

At 1540, the source spinal image may be analyzed. In some embodiments, the data processing component (e.g., a server(s)) may initiate an image analysis with respect to the source spinal image. The data processing component may include one or more distributed analysis subcomponents. When the data processing component includes multiple distributed analysis subcomponents, at 1545, load distribution processing may be performed with respect to multiple source spinal images. For example, at 1550, a source spinal image or a part thereof may be provided to a distributed analysis subcomponent for a particular analysis.

According to various embodiments, if the data processing component includes multiple distributed analysis subcomponents, e data processing component may perform analytical processing with respect to multiple source images (e.g., source spinal images). In some embodiments, in connection with improving the quality and efficiency of analytical processing of multiple source spinal images, the load information corresponding to each distributed analysis subcomponent may be obtained and load distribution may be performed with respect to multiple source spinal images based at least in part on load information corresponding to each distributed analysis subcomponent. As an example, distributed analysis subcomponents with smaller information loads may be allocated a greater number source spinal images for analytical processing and distributed analysis subcomponents with greater information loads may be allocated a smaller number of source spinal images for analytical processing. The load distribution according to various embodiments effectively ensures the quality and efficiency of analytical processing conducted on multiple source spinal images while improving accuracy and reliability in acquiring processing results corresponding to multiple source spinal images.

The analysis performed based on the distributed analysis subcomponent may be combined and/or aggregated in connection with performing analytical processing results with respect to multiple source spinal images through distributed analysis subcomponents.

At 1555, the analytical processing results are communicated to the IT component. For example, the analytical processing results may be communicated so that the IT component may display the analytical processing results.

Figure 16:
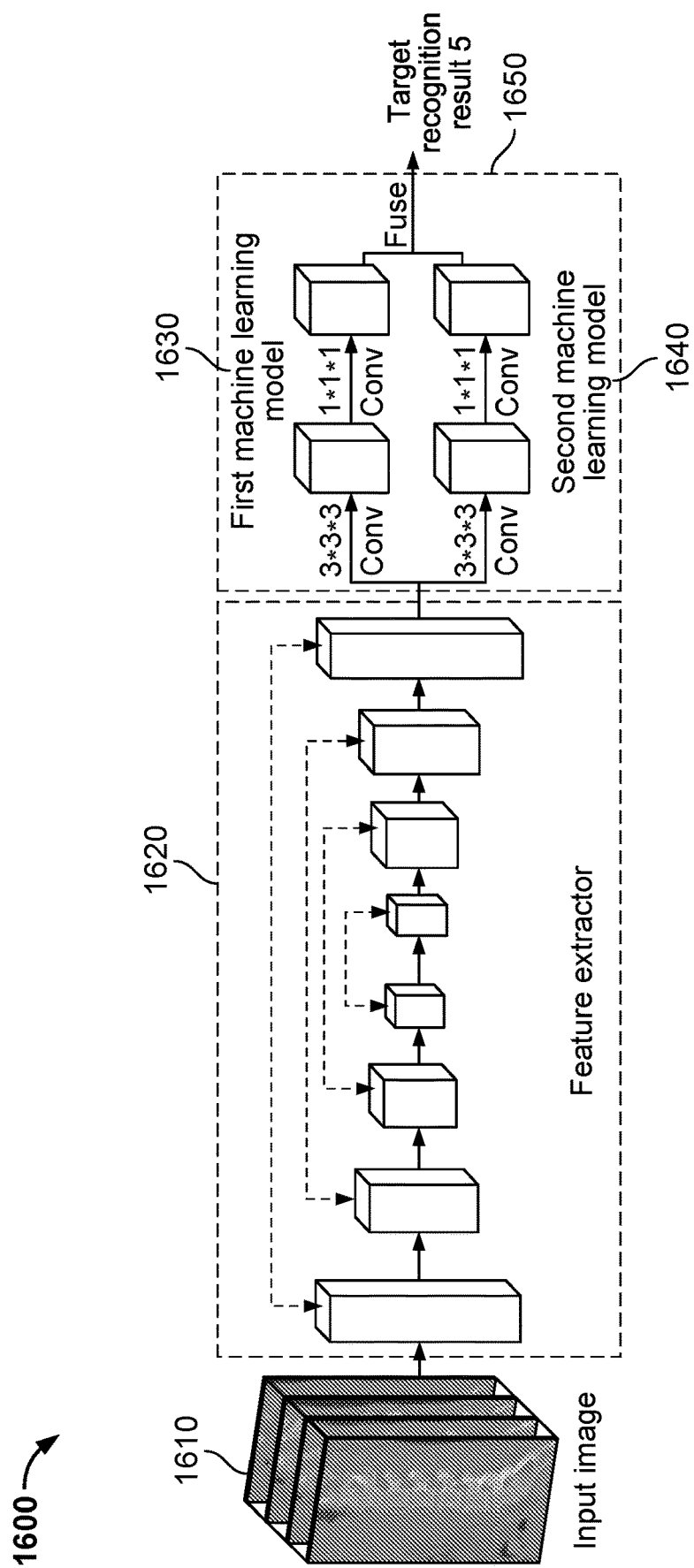
FIG. 16 is a diagram of illustrating a method for processing a spinal image according to various embodiments of the present application.

FIG. 16 is a diagram of illustrating a method for processing a spinal image according to various embodiments of the present application.

Referring to FIG. 16, process 1600 may be implemented by a terminal. For example, process 1600 may be implemented by an image capturing device such as a mobile phone, a tablet, etc. As another example, process 1600 may be implemented in connection with medical imaging (e.g., by a terminal or server associated with processing images captured by a medical device such as an x-ray, an magnetic resonance imaging (MM), etc.). Process 1600 may be implemented in connection with other imaging/image capturing technologies. Process 1600 may be implemented by one or more servers that perform image processing and/or analysis with respect to one or more source images. According to various embodiments, process 1600 is performed in response to a user input with respect to the source spinal image or corresponding target recognition results. For example, a terminal or server implements process 1600 based at least in part on a user input with respect to an execution operation.

As illustrated in FIG. 16, in connection with a data processing component (e.g., one or more servers) performing an analytical processing with respect to a source spinal image, the process 1600 may include feature extraction operations carried out by a feature extractor on the input source spinal image and analytical processing operations carried out by a first machine learning model and a second machine learning model on the extracted image features.

At 1610, a source spinal image is input into the feature extractor.

At 1620, image features corresponding to the source spinal image is obtained. In some embodiments, a feature extractor is connection with obtaining image features corresponding to the source spinal image. The image features may include position features of pixels in the source spinal image and pathologic type features corresponding to pixels in the source spinal image.

The feature extractor may be a feature extraction network capable of capturing multidimensional features. In some embodiments, because the V-Net medical image segmentation network can preserve both high-level semantic information and low-level image details, the V-Net medical image segmentation network can be used as a feature extractor. In addition, V-Net can employ a codec mode. The image features output by its decoder (i.e., the results output by the feature extractor) can have the same resolution as the to-be-processed spinal image. The V-Net medical image segmentation network may be a convolution neural network for image segmentation (e.g., 3D image segmentation).

At 1630, the obtained image features are input into a first machine learning model. The first machine learning model may be used in connection with obtaining vertebral body positions corresponding to the vertebral bodies included in the source spinal image and intervertebral disc positions corresponding to the intervertebral discs.

According to various embodiments, the first machine learning model is pre-trained or generated. The first machine learning model may obtain training images. The training images may include vertebral body center positions corresponding to two or more vertebral bodies, and intervertebral disc center positions corresponding to two or more intervertebral discs. The vertebral body center positions corresponding to two or more vertebral bodies and intervertebral disc center positions corresponding to two or more intervertebral discs may conform to a Gaussian distribution.

In some embodiments, the vertebral body center positions corresponding to two or more vertebral bodies and the intervertebral disc center positions corresponding to two or more intervertebral discs as supervisory signals may be used to train and generate a first machine learning model. The number of data channels of the first machine learning model may be 2. A first data channel may be used to label a pixel as not being a vertebral body center position/intervertebral disc center position, and a second data channel may be used to label a pixel as being a vertebral body center position/intervertebral disc center position.

After being generated, the first machine learning model may be used to recognize the first probability of each pixel in an image feature being a vertebral body center position, and the second probability of each pixel being an intervertebral disc center position. The first machine learning model may then be used to determine the points with the greatest local probability as the vertebral body center position and the intervertebral disc center position.

At 1640, the obtained image features are input into the second machine learning model. In some embodiments, the second machine learning model is used to determine the vertebral body recognition results corresponding to the vertebral bodies and the intervertebral disc recognition results corresponding to the intervertebral discs.

According to various embodiments, the second machine learning model is pre-trained or generated. The second machine learning model may obtain a training image. The training image may include vertebral body center positions corresponding to two or more vertebral bodies, intervertebral disc center positions corresponding to two or more intervertebral discs, vertebral body pathologic types corresponding to vertebral body center positions, and intervertebral disc pathologic types corresponding to intervertebral disc center positions. Determine the region (e.g., circular region, oval region, spherical region, etc.) having the vertebral body center position/intervertebral disc center position as its center and R (e.g., 6) as the center radius of the region, and determine the region as the vertebral body training region/intervertebral disc training region. Then use vertebral body training regions, intervertebral disc training regions, vertebral body pathologic types corresponding to vertebral body center positions, and intervertebral disc pathologic types corresponding to intervertebral disc center positions as supervisory signals to train and generate a second machine learning model. When the vertebral bodies comprise lumbar vertebral bodies, the number of data channels of the second machine learning model may be 9. The 9 data channels may correspond to 7 types of intervertebral disc degenerative disease and to 2 types of vertebral body degenerative disease, and probability maps are generated with the same resolution as the image features.

After the second machine learning model is generated, the second machine learning model may be used to determine vertebral body recognition results corresponding to the vertebral bodies and intervertebral disc recognition results corresponding to the intervertebral discs. In some embodiments, the second machine learning model may be used to obtain third probabilities of vertebral body center positions corresponding to all vertebral body pathologic types and to determine the vertebral body pathologic type having the largest local probability as the vertebral body recognition result corresponding to the vertebral body center position. The second machine learning model may be used to obtain fourth probabilities of intervertebral disc center positions corresponding to all intervertebral disc pathologic types, and then to determine the intervertebral disc pathologic type having the greatest local probability as the intervertebral disc recognition result corresponding to intervertebral disc center position.

At 1650, target recognition results corresponding to the source spinal image is determined based on the vertebral body recognition results and intervertebral disc recognition results. In addition, according to various embodiments, the target recognition results corresponding to the source spinal image may be displayed.

Various embodiments provide a method for processing a spinal image end-to-end spinal image. According to various embodiments, the image processing method uses convolutional neural networks in connection with processing the images. Various embodiments effectively achieve recognition of vertebral bodies and intervertebral discs without having to segment the source spinal image. This approach not only decreases the number of data processing steps and reduces data processing volume, but also, with this method, batch processing of multiple source spinal images may be implemented, thus helping to alleviate the primary care supply-demand imbalance while also improving the quality and efficiency of to-be-processed spinal image analytical processing and further increasing the utility of the method to the benefit of market promotions and applications.

Figure 17:
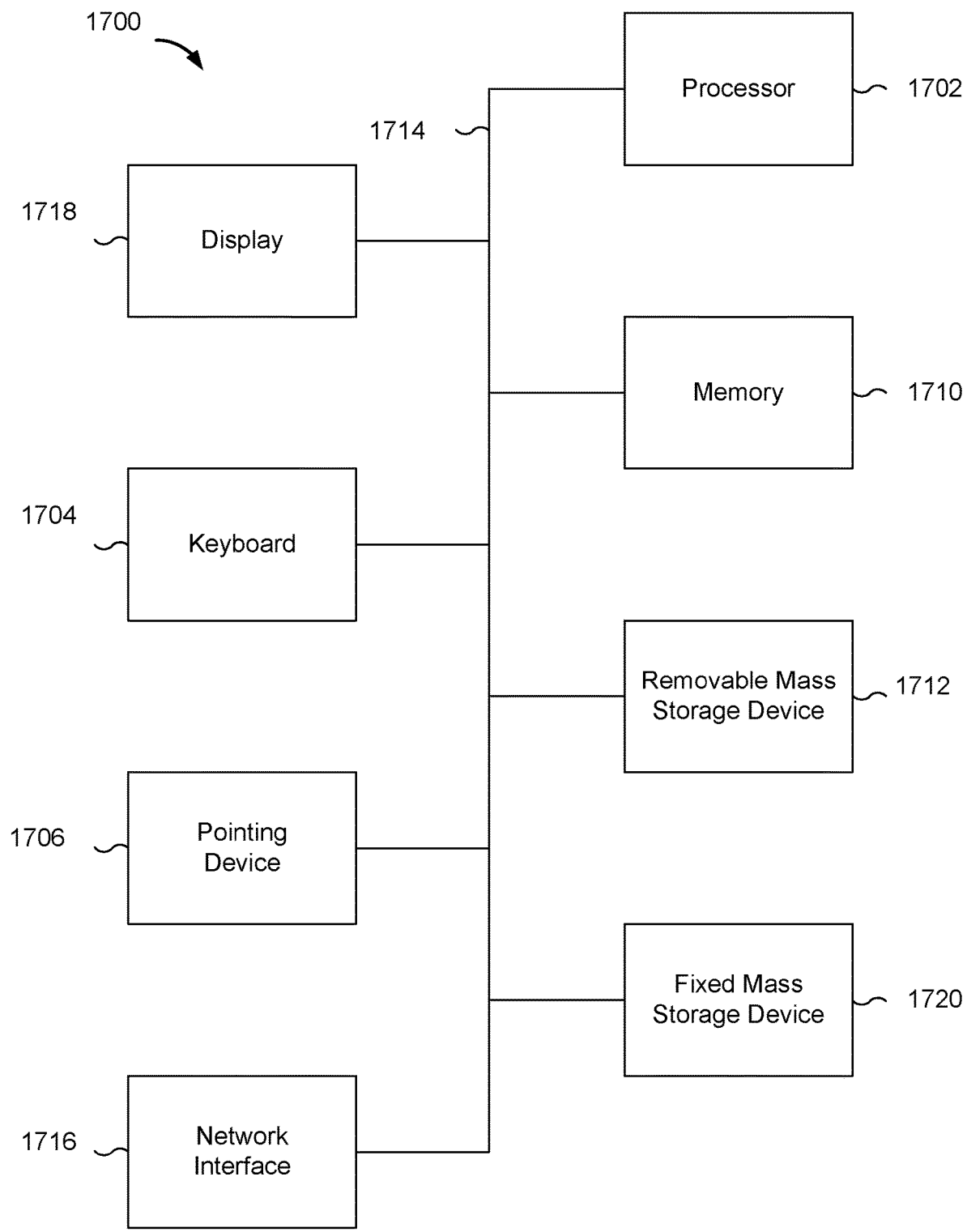
FIG. 17 is a functional diagram of a computer system according to various embodiments of the present application.

FIG. 17 is a functional diagram of a computer system according to various embodiments of the present application.

Computer system 1700 may implement process 100 of FIG. 1, process 400 of FIG. 4, process 500 of FIG. 5, process 600 of FIG. 6, process 700 of FIG. 7, process 800 of FIG. 8, process 900 of FIG. 9, process 1000 of FIG. 10, process 1100 of FIG. 11, process 1200 of FIG. 12, process 1300 of FIG. 13, process 1400 of FIG. 14, process 1500 of FIG. 15, and/or process 1600 of FIG. 16.

Processor 1702 is coupled bi-directionally with memory 1710, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 1702. Also as is well known in the art, primary storage typically includes basic operating instructions, program code, data, and objects used by the processor 1702 to perform its functions (e.g., programmed instructions). For example, memory 1710 can include any suitable computer-readable storage media, described below, depending on whether, for example, data access needs to be bi-directional or uni-directional. For example, processor 1702 can also directly and very rapidly retrieve and store frequently needed data in a cache memory (not shown). The memory can be a non-transitory computer-readable storage medium.

A removable mass storage device 1712 provides additional data storage capacity for the computer system 1700, and is coupled either bi-directionally (read/write) or uni-directionally (read only) to processor 1702. For example, storage 1712 can also include computer-readable media such as magnetic tape, flash memory, PC-CARDS, portable mass storage devices, holographic storage devices, and other storage devices. A fixed mass storage 1720 can also, for example, provide additional data storage capacity. The most common example of mass storage 1720 is a hard disk drive. Mass storage device 1712 and fixed mass storage 1720 generally store additional programming instructions, data, and the like that typically are not in active use by the processor 1702. It will be appreciated that the information retained within mass storage device 1712 and fixed mass storage 1720 can be incorporated, if needed, in standard fashion as part of memory 1710 (e.g., RAM) as virtual memory.

In addition to providing processor 1702 access to storage subsystems, bus 1714 can also be used to provide access to other subsystems and devices. As shown, these can include a display monitor 1718, a network interface 1716, a keyboard 1704, and a pointing device 1706, as well as an auxiliary input/output device interface, a sound card, speakers, and other subsystems as needed. For example, the pointing device 1706 can be a mouse, stylus, track ball, or tablet, and is useful for interacting with a graphical user interface.

The network interface 1716 allows processor 1702 to be coupled to another computer, computer network, or telecommunications network using a network connection as shown. For example, through the network interface 1716, the processor 1702 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 1702 can be used to connect the computer system 1700 to an external network and transfer data according to standard protocols. For example, various process embodiments disclosed herein can be executed on processor 1702, or can be performed across a network such as the Internet, intranet networks, or local area networks, in conjunction with a remote processor that shares a portion of the processing. Additional mass storage devices (not shown) can also be connected to processor 1702 through network interface 1716.

An auxiliary I/O device interface (not shown) can be used in conjunction with computer system 1700. The auxiliary I/O device interface can include general and customized interfaces that allow the processor 1702 to send and, more typically, receive data from other devices such as microphones, touch-sensitive displays, transducer card readers, tape readers, voice or handwriting recognizers, biometrics readers, cameras, portable mass storage devices, and other computers.

The computer system shown in FIG. 17 is but an example of a computer system suitable for use with the various embodiments disclosed herein. Other computer systems suitable for such use can include additional or fewer subsystems. In addition, bus 1714 is illustrative of any interconnection scheme serving to link the subsystems. Other computer architectures having different configurations of subsystems can also be utilized.

The systems, means, modules, or units illustrated by the above embodiments specifically may be implemented by computer chips or entities or by products having certain functions. A typical implementing device is a computer. The particular form a computer may take may be a personal computer, laptop computer, cellular phone, camera phone, smart phone, personal digital assistant, media player, navigation device, email receiving device, game console, tablet computer, wearable device, or a combination of any of these devices.

In a typical configuration, a computer comprises one or more processors (CPUs), input/output ports, network interfaces, and memory.

Memory may include the following forms in computer-readable media: volatile memory, random access memory (RAM), and/or non-volatile memory, e.g., read-only memory (ROM) or flash RAM. Memory is an example of a computer-readable medium.

Each of the embodiments contained in this specification is described in a progressive manner. The explanation of each embodiment focuses on areas of difference from the other embodiments, and the descriptions thereof may be mutually referenced regarding portions of each embodiment that are identical or similar.

A person skilled in the art should understand that an embodiment of the present application may provide methods, devices, or computer program products. Therefore, the embodiments of the present application may take the form of embodiments that are entirely hardware, embodiments that are entirely software, and embodiments that combine hardware and software aspects. Moreover, an embodiment of the present application may take the form of one or more computer program products implemented on computer-usable storage media (including but not limited to magnetic disk memory, CD-ROM, and optical memory) containing computer-usable program code.

The memory in each of the embodiments described above may take the form of any type of volatile or non-volatile storage device or combination thereof, such as static random access memory (SRAM), electrically erasable programmable read-only memory (EEPROM), erasable programmable read-only memory (EPROM), programmable read-only memory (PROM), read-only memory (ROM), magnetic memory, flash memory, magnetic disks, or optical disks.

Computer system 1700 may comprise a communication interface and/or commination component. The communication component may be configured to facilitate wired or wireless communication between the device on which the communication component is located (e.g., computer system 1700) and other devices (e.g., an access point or a terminal connected to a network, etc.). The device on which the communication component is located (e.g., computer system 1700) may access wireless networks based on a communications standard such as WiFi, 2G, 3G, 4G/LTE, 5G, or another mobile communications network or a combination thereof. In an exemplary embodiment, the communication component receives via broadcast channels broadcast signals or broadcast-related information from external broadcast management systems. In some embodiments, the communication component further comprises a near-field communication (NFC) module for promoting short-range communication. For example, communication can be achieved in the NFC module on the basis of radio-frequency identification (RFID) technology, Infrared Data Association (IrDA) technology, ultra-wide band (UWB) technology, Bluetooth (BT) technology, and other technology.

The display in each of the embodiments described above comprises a screen, and the screen may comprise a liquid crystal display (LCD) or touch panel (TP). If the screen comprises a touch panel, the screen may be implemented as a touchscreen to receive input signals from the user. The touch panel comprises one or more touch sensors to detect touch, swipe actions, and gestures on the touch panel. Said touch sensor not only can detect the boundaries of touch or swipe actions, but also can measure the duration and pressure related to said touch or swipe operations.

The power supply component in each of the embodiment described above is for providing electric power to all components in the device where the power supply component is located. The power supply component may include a power supply management system, one or more power supplies, and other components related to generating, managing, and allocating power to the device where the power supply component is located.

The audio component in each of the embodiments described above may be configured to output and/or input audio signals. For example, the audio component includes a microphone (MIC). When the device where the audio component is located is in an operating mode, e.g., when in calling mode, recording mode, or speech recognition mode, the microphone is configured to receive external audio signals. The received audio signals may be further stored in memory or sent by the communication component. In some embodiments, the audio component further comprises a speaker for outputting audio signals.

A person skilled in the art should understand that the embodiment of the present application can be provided as methods, systems or computer software products. Therefore, the present application may take the form of complete hardware embodiments, complete software embodiments, or embodiments that combine software and hardware. In addition, the present application can take the form of computer program products implemented on one or more computer-operable storage media (including but not limited to magnetic disk storage devices, CD-ROMs, and optical storage devices) containing computer operable program code.

The present application is described with reference to flowcharts and/or block diagrams based on methods, devices (systems), and computer program products of embodiments of the present application. Please note that each process and/or block within the flowcharts and/or block diagrams and combinations of processes and/or blocks within the flowcharts and/or block diagrams can be implemented by computer instructions. These computer program instructions can be provided to general-purpose computers, special-purpose computers, embedded processors, or processors of other data-processing devices to give rise to a machine such that the instructions by the computers or by the processors of other programmable data-processing devices give rise to devices used to implement the functions specified in one or more processes in a flowchart and/or in one or more blocks in a block diagram.

These computer program instructions can also be stored in computer-readable memory that can guide computers or other programmable data-processing devices to operate according to specific modes, with the result that the instructions stored in this computer-readable memory give rise to products that include command means. These command means implement the functions specified in one or more processes in a flow chart and/or one or more blocks in a block diagram.

These computer program instructions can also be loaded onto a computer or other programmable data-processing device, with the result that a series of operating steps are executed on a computer or other programmable device so as to give rise to computer processing. In this way, the instructions executed on a computer or other programmable device provide steps for implementing the functions specified by one or more processes in a flow chart and/or one or more blocks in a block diagram.

Computer-readable media, including permanent and non-permanent and removable and non-removable media, may achieve information storage by any method or technology. The information may be computer-readable instructions, data structures, program modules, or other data. Examples of computer storage media include but are not limited to phase-change memory (PRAM), static random access memory (SRAM), dynamic random access memory (DRAM), other types of random access memory (RAM), read-only memory (ROM), electrically erasable programmable read-only memory (EEPROM), flash memory or other memory technology, compact disk read-only memory (CD-ROM), digit multifunction disc (DVD) or other optical storage, magnetic cassettes, magnetic tape or magnetic disc storage, or other magnetic storage equipment or any other non-transmission media that can be used to store information that is accessible to computers. In accordance with the definitions in this document, computer-readable media do not include transitory computer-readable media (transitory media) such as modulated data signals and carrier waves.

In addition, some of the processes described in the above embodiments and drawings contain multiple operations which appear according to a specific sequence. However, one must understand fully that these operations may be executed according to a sequence other than the one that appears in the text or may be executed in parallel. Operation sequence numbers such as 102 and 103 merely serve to differentiate the different operations from each other. The sequence numbers themselves do not represent any sequence of execution. In addition, these processes may include more or fewer operations, and these operations may be executed sequentially or in parallel. Please note that the descriptors "first," "second," and so on are for differentiating different messages, devices, modules, and so on and do not represent a sequence, nor do "first" and "second" limit them to different types.

The means embodiments described above are merely for the purpose of example. The units described therein as separate components may or may not be physically separate, and components displayed as units may or may not be physical units. They can be located in one place, or they can be distributed across multiple network units. Some or all of the modules herein may be chosen according to actual need to achieve the objectives of the present embodiments. A person with ordinary skill in the art may understand and implement them without expending creative effort.

Through descriptions of the above implementations, persons skilled in the art can clearly understand that the implementations may be realized with the necessary general-use hardware platform. Of course, they may also be realized through combinations of hardware and software. On the basis of such an understanding, the technical scheme described above, whether essentially or in those parts that contribute to the prior art, may be embodied in the form of computer products. The present invention may take the form of one or more computer program products implemented on computer-usable storage media (including but not limited to magnetic disk memory, CD-ROM, and optical memory) containing computer-usable program code.

According to various embodiments, a method for training a learning model is provided. In some embodiments, the method includes obtaining a training image, wherein the training image comprises one or more vertebral bodies, intervertebral discs, at least two standard vertebral body positions corresponding to the one or more vertebral bodies, and at least two standard intervertebral disc positions corresponding to the one or more intervertebral discs. In some embodiments, the method further includes performing a learning training based at least in part on the one or more vertebral bodies, at least two standard vertebral body positions, the one or more intervertebral discs, and at least two standard intervertebral disc positions included in the training image to generate a first machine learning model, the machine learning model being used in connection with determining vertebral body positions corresponding to the one or more vertebral bodies and intervertebral disc positions corresponding to the one or more intervertebral discs in a spinal image. In some embodiments, at least two standard vertebral body positions may conform to a Gaussian distribution in the training image. In some embodiments, at least two standard intervertebral disc positions conform to a Gaussian distribution in the training image.

According to various embodiments, a method for training a learning model is provided. In some embodiments, the method includes obtaining, by one or more processors, a training image, wherein the training image comprises vertebral body positions corresponding to one or more vertebral bodies, intervertebral disc positions corresponding to one or more intervertebral discs, vertebral body pathologic types corresponding to the one or more vertebral bodies, and intervertebral disc pathologic types corresponding to the one or more intervertebral discs. In some embodiments, the method further includes performing, by the one or more processors, a learning training based at least in part on the vertebral body positions corresponding to the one or more vertebral bodies, intervertebral disc positions corresponding to the one or more intervertebral discs, vertebral body pathologic types corresponding to the one or more vertebral bodies, and intervertebral disc pathologic types corresponding to the one or more intervertebral discs to obtain a second machine learning model, wherein the second machine learning model is used in connection with determining vertebral body recognition results corresponding to one or more vertebral bodies and intervertebral disc recognition results corresponding to the one or more intervertebral discs in a spinal image.

In some embodiments, the performing learning training to obtain the second machine learning model comprises: obtaining vertebral body regions corresponding to the vertebral body positions and intervertebral disc regions corresponding to the intervertebral disc positions; and performing learning training with respect to vertebral body regions, vertebral body pathologic types, intervertebral disc regions, and intervertebral disc pathologic types to obtain the second machine learning model. In some embodiments, the obtaining vertebral body regions corresponding to the vertebral body positions comprises obtaining a first radius for determining the vertebral body region; and determining the region within the first radius centered at the vertebral body position as the vertebral body region. In some embodiments, the obtaining intervertebral disc regions corresponding to the intervertebral disc positions comprises: obtaining a second radius for determining the intervertebral disc region; and determining the region within the second radius centered at the intervertebral disc position as said intervertebral disc region.

According to various embodiments a device (or terminal) is provided. The device may include one or more processors, and a memory, for storing a program for training methods, wherein in response to execution program. In some embodiments, in response to execution program, the one or more processors are caused to: obtaining a training image, wherein the training image comprises one or more vertebral bodies, intervertebral discs, at least two standard vertebral body positions corresponding to the one or more vertebral bodies, and at least two standard intervertebral disc positions corresponding to the one or more intervertebral discs; and performing a learning training based at least in part on the one or more vertebral bodies, at least two standard vertebral body positions, the one or more intervertebral discs, and at least two standard intervertebral disc positions included in the training image to generate a first machine learning model, the machine learning model being used in connection with determining vertebral body positions corresponding to the one or more vertebral bodies and intervertebral disc positions corresponding to the one or more intervertebral discs in a spinal image.

According to various embodiments a device (or terminal) is provided. The device may include one or more processors, and a memory, for storing a program for training methods, wherein in response to execution program. In some embodiments, in response to execution program, the one or more processors are caused to: obtaining, by one or more processors, a training image, wherein the training image comprises vertebral body positions corresponding to one or more vertebral bodies, intervertebral disc positions corresponding to one or more intervertebral discs, vertebral body pathologic types corresponding to the one or more vertebral bodies, and intervertebral disc pathologic types corresponding to the one or more intervertebral discs; and performing, by the one or more processors, a learning training based at least in part on the vertebral body positions corresponding to the one or more vertebral bodies, intervertebral disc positions corresponding to the one or more intervertebral discs, vertebral body pathologic types corresponding to the one or more vertebral bodies, and intervertebral disc pathologic types corresponding to the one or more intervertebral discs to obtain a second machine learning model, wherein the second machine learning model is used in connection with determining vertebral body recognition results corresponding to one or more vertebral bodies and intervertebral disc recognition results corresponding to the one or more intervertebral discs in a spinal image.

The final point that should be explained is the following: the above embodiments only serve to explain the technical schemes of the present invention and not to limit it. Although the present invention was explained in detail with reference to the above-described embodiments, persons skilled in the art should understand that they may modify the technical schemes recorded in the various embodiments described above or provide equivalent substitutions for some of their technical features. Yet these modifications or substitutions do not cause the corresponding technical schemes to substantively depart from the spirit and scope of the technical schemes of the various embodiments of the present invention.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
    obtaining, by one or more processors, a source spinal image;
    identifying, by the one or more processors, one or more vertebral bodies and one or more intervertebral discs comprised in the source spinal image;
    determining, by the one or more processors, the vertebral body recognition results corresponding to the one or more vertebral bodies and the intervertebral disc recognition results corresponding to the one or more intervertebral discs;
    determining, by the one or more processors, target recognition results corresponding to the source spinal image based at least in part one on one or more of the vertebral body recognition results and the intervertebral disc recognition results; and
    providing, by the one or more processors, the target recognition results corresponding to the source spinal image, the providing the target recognition results comprising causing at least part of the target recognition results to be displayed on a user interface of a client terminal.

2. The method of claim 1, wherein the identifying the one or more vertebral bodies and the one or more intervertebral discs included in the source spinal image comprises:
    obtaining vertebral body positions corresponding to the vertebral bodies comprised in the source spinal image and intervertebral disc positions corresponding to the intervertebral discs;
    determining the one or more vertebral bodies comprised in the source spinal image based at least in part on the vertebral body positions; and
    determining the one or more intervertebral discs included in said to-be-processed spinal image based at least in part on the intervertebral disc positions.

3. The method of claim 2, wherein the obtaining vertebral body positions corresponding to the one or more vertebral bodies included in the source spinal image, and intervertebral disc positions corresponding to the one or more intervertebral discs comprises:
    obtaining image features corresponding to the source spinal image, the image features comprising position features of pixels in the source spinal image; and
    determining vertebral body positions corresponding to the one or more vertebral bodies included in the source spinal image and intervertebral disc positions corresponding to the one or more intervertebral discs based at least in part on one or more image features.

4. The method of claim 3, wherein the determining vertebral body positions corresponding to the one or more vertebral bodies included in the source spinal image and intervertebral disc positions corresponding to the one or more intervertebral discs based at least in part on one or more image features comprises:
    using a first convolutional neural network in connection with performing analytical processing of the one or more image features, and obtaining vertebral body positions corresponding to vertebral bodies comprised in the source spinal image and intervertebral disc positions corresponding to the one or more intervertebral discs, wherein:
        the first convolutional neural network is trained for determining vertebral body positions corresponding to vertebral bodies and intervertebral disc positions corresponding to the intervertebral discs in the spinal image.

5. The method of claim 4, wherein the using a first convolutional neural network in connection with performing obtaining processing and acquiring vertebral body positions corresponding to the vertebral bodies comprised in the source spinal image and intervertebral disc positions corresponding to the one or more intervertebral discs comprises:
    using the first convolutional neural network in connection with performing an analytical processing with respect to the one or more image features and, for each pixel in the source spinal image, obtaining a first probability of the corresponding pixel being a vertebral body position and a second probability of the corresponding pixel being an intervertebral disc position;
    determining vertebral body positions corresponding to the one or more vertebral bodies based at least in part on the first probabilities corresponding to all pixels in the source spinal image; and
    determining intervertebral disc positions corresponding to the one or more intervertebral discs based at least in part on the second probabilities corresponding to all pixels in the source spinal image.

6. The method of claim 5, wherein the determining vertebral body positions corresponding to the one or more vertebral bodies based at least in part on the first probabilities corresponding to the pixels in the source spinal image comprises:
   determining the position information corresponding to the pixel for which a first probability is the greatest of all of a set of the pixels as the vertebral body position corresponding to the vertebral body.

7. The method of claim 5, wherein the determining intervertebral disc positions corresponding to the one or more intervertebral discs based at least in part on the second probabilities corresponding to all of a set of the pixel in the source spinal image comprises:
   determining the position information corresponding to the pixel for which the second probability is the greatest of all the set of the pixels as the intervertebral disc position corresponding to the intervertebral disc.

8. The method of claim 2, wherein determining vertebral bodies comprised in the source spinal image based at least in part on the vertebral body positions comprises:
   determining the vertebral body positions as vertebral bodies included in the source spinal image, or
   obtaining a first preset regions including the vertebral body positions, and determining the first preset regions to correspond to vertebral bodies included in the source spinal image.

9. The method of claim 2, wherein the determining intervertebral discs included in the source spinal image based at least in part on the intervertebral disc positions comprises:
   determining the intervertebral disc positions as intervertebral discs comprised in the source spinal image, or
   obtaining second preset regions including the intervertebral disc positions, and determining the second preset regions as intervertebral discs included in the source spinal image.

10. The method of claim 3, wherein:
    the one or more image features comprise pathologic-type features corresponding to pixels in the source spinal image; and
    the determining vertebral body recognition results corresponding to the one or more vertebral bodies and intervertebral disc recognition results corresponding to the intervertebral discs comprises:
       using a second convolutional neural network in connection with performing an analytical processing with respect to the one or more image features, and obtaining vertebral body recognition results corresponding to the one or more vertebral bodies and intervertebral disc recognition results corresponding to the one or more intervertebral discs,
       wherein the second convolutional neural network is trained for determining vertebral body recognition results corresponding to vertebral bodies and intervertebral disc recognition results corresponding to the intervertebral discs in the source spinal image.

11. The method of claim 10, wherein the using the second convolutional neural network in connection with performing an analytical processing with respect to the one or more image features, and obtaining vertebral body recognition results corresponding to the one or more vertebral bodies and intervertebral disc recognition results corresponding to the one or more intervertebral discs comprises:
    using the second convolutional neural network in connection with performing an analytical with respect to the one or more image features, and obtaining third probabilities of vertebral body positions corresponding to different preset vertebral body recognition types and fourth probabilities of intervertebral disc positions corresponding to different preset intervertebral disc recognition types in the source spinal image;
    determining vertebral body recognition results corresponding to the one or more vertebral bodies based on the third probabilities of the vertebral body positions corresponding to at least a set of preset vertebral body recognition types; and
    determining intervertebral disc recognition results corresponding to the one or more intervertebral discs based on the fourth probabilities of the intervertebral disc positions corresponding to at least a set of preset intervertebral disc recognition types.

12. The method of claim 11, wherein the determining the vertebral body recognition results corresponding to the one or more vertebral bodies based at least in part on the third probabilities of the vertebral body positions corresponding to the at least the set of preset vertebral body recognition types comprises:
    determining the preset vertebral body recognition type for which the third probability is the greatest of all preset vertebral body recognition types as the vertebral body recognition result corresponding to the vertebral body.

13. The method of claim 11, wherein the determining the intervertebral disc recognition results corresponding to the one or more intervertebral discs based at least in part on the fourth probabilities of the intervertebral disc positions corresponding to all preset intervertebral disc recognition types comprises:
    determining the preset intervertebral disc recognition type for which the fourth probability is the greatest of the at least the set of preset intervertebral disc recognition types as the intervertebral disc recognition result corresponding to the intervertebral disc.

14. The method of claim 11, wherein:
    the one or more vertebral bodies comprise at least one of the following: spinal vertebral bodies, thoracic vertebral bodies, and lumbar vertebral bodies;
    if the one or more vertebral bodies comprise lumbar vertebral bodies, the preset vertebral body recognition types comprise at least one of the following: normal vertebral body and vertebral body with degenerative change, and preset intervertebral disc recognition types comprise at least one of the following: normal intervertebral disc and pathologic change of intervertebral disc;
    the pathologic change of intervertebral disc comprises at least one of the following: intervertebral disc bulge and intervertebral disc herniation;
    the intervertebral disc bulge comprises at least one of the following: diffuse intervertebral disc bulge and asymmetric intervertebral disc bulge; and
    the intervertebral disc herniation comprises at least one of the following: intervertebral disc protrusion, intervertebral disc extrusion, intervertebral disc sequestration, and intervertebral herniation.

15. The method of claim 1, wherein the one or more vertebral bodies comprise at least one of the following: spinal vertebral bodies, thoracic vertebral bodies, and lumbar vertebral bodies.

16. The method of claim 1, wherein target recognition results comprise a probability map having a same resolution as the source spinal image, the probability map comprising vertebral body recognition probabilities corresponding to the vertebral body recognition results and intervertebral disc recognition probabilities corresponding to the intervertebral disc recognition results.

17. The method of claim 1, further comprising:
displaying the source spinal image and the corresponding target recognition results;
obtaining one or more user inputs that are input by the user and directed at the target recognition results; and
performing corresponding processing operations based at least in part on the one or more user inputs directed at the target recognition results.

18. The method of claim 17, wherein, after performing corresponding processing operations based at least in part on the one or more user inputs directed at the target recognition results, further comprising:
obtaining a processing result corresponding to the processing operation; and
in response to a determination that the processing result differs from the target recognition result, updating the second convolutional neural network based at least in part on the processing result and the target recognition result,
wherein the second convolutional neural network is trained for determining vertebral body recognition results corresponding to vertebral bodies and intervertebral disc recognition results corresponding to the intervertebral discs in the spinal image, the vertebral body recognition results and the intervertebral disc recognition results being related to the target recognition results.

19. The method of claim 1, wherein the determining the target recognition results comprises performing a pixel-by-pixel analysis of a representation of the source spinal image to determine whether a particular pixel comprises an abnormality.

20. A device, comprising:
one or more processors; and
a memory, for storing a program for image processing methods, wherein in response to execution program, the one or more processors are caused to:
obtaining a source spinal image;
identifying one or more vertebral bodies and one or more intervertebral discs comprised in the source spinal image;
determining the vertebral body recognition results corresponding to the one or more vertebral bodies and the intervertebral disc recognition results corresponding to the one or more intervertebral discs;
determining target recognition results corresponding to the source spinal image based at least in part one on one or more of the vertebral body recognition results and the intervertebral disc recognition results; and
providing the target recognition results corresponding to the source spinal image, the providing the target recognition results comprising causing at least part of the target recognition results to be displayed on a user interface of a client terminal.

21. A computer program product, the computer program product being embodied in a non-transitory computer readable storage medium and comprising computer instructions for:
obtaining a source spinal image;
identifying one or more vertebral bodies and one or more intervertebral discs comprised in the source spinal image;
determining the vertebral body recognition results corresponding to the one or more vertebral bodies and the intervertebral disc recognition results corresponding to the one or more intervertebral discs;
determining target recognition results corresponding to the source spinal image based at least in part one on one or more of the vertebral body recognition results and the intervertebral disc recognition results; and
providing the target recognition results corresponding to the source spinal image, the providing the target recognition results comprising causing at least part of the target recognition results to be displayed on a user interface of a client terminal.

* * * * *